US006920196B2

United States Patent
Ueno et al.

(10) Patent No.: US 6,920,196 B2
(45) Date of Patent: Jul. 19, 2005

(54) RADIOLOGICAL IMAGING APPARATUS

(75) Inventors: Yuuichirou Ueno, Hitachi (JP); Kensuke Amemiya, Hitachinaka (JP); Shinichi Kojima, Hitachi (JP); Takashi Okazaki, Hitachinaka (JP); Kikuo Umegaki, Hitachinaka (JP); Hiroshi Kitaguchi, Naka-machi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/253,492

(22) Filed: Sep. 25, 2002

(65) Prior Publication Data
US 2003/0118155 A1 Jun. 26, 2003

(30) Foreign Application Priority Data

Dec. 26, 2001 (JP) ........................................ 2001-393044

(51) Int. Cl.⁷ .............................................. G01T 1/166
(52) U.S. Cl. .................................... 378/19; 250/363.03
(58) Field of Search ............................ 378/19, 4, 5, 20; 250/363.03, 367, 363.04, 363.05, 363.06, 363.02, 370.06, 370.08, 370.09; 600/427, 431, 436

(56) References Cited

U.S. PATENT DOCUMENTS

| | | | | |
|---|---|---|---|---|
| 6,448,559 B1 | * | 9/2002 | Saoudi et al. | 250/367 |
| 6,449,331 B1 | * | 9/2002 | Nutt et al. | 378/19 |
| 6,490,476 B1 | * | 12/2002 | Townsend et al. | 600/427 |
| 6,631,284 B2 | * | 10/2003 | Nutt et al. | 600/427 |
| 6,661,866 B1 | * | 12/2003 | Limkeman et al. | 378/19 |

FOREIGN PATENT DOCUMENTS

| EP | 1 271 181 A2 | 1/2003 |
|---|---|---|
| JP | 09005441 | 10/1997 |
| WO | WO 97/20232 | 6/1997 |

OTHER PUBLICATIONS

Iwata K., et al., "Description of a Prototype Combined CT–SPECT System with a Single CdZnTe Detector," Nuclear Science Symposium Conference Record, 2001 IEEE.

Saoudi, A., et al., "A Novel APD–Based Detector Module for Multi–Modality PET/SPECT/CT Scanners," Nuclear Science Symposium, 1998. 1999 IEEE.

* cited by examiner

*Primary Examiner*—David V. Bruce
*Assistant Examiner*—Hoon Song
(74) *Attorney, Agent, or Firm*—Dickstein Shapiro Morin & Oshinsky LLP

(57) ABSTRACT

An imaging apparatus of a radiological imaging apparatus is provided with a first and a second radiation detectors disposed around a hole portion into which a bed is inserted. The first radiation detector includes a detecting portion formed of GaAs of a square having a side of 5 mm and having a thickness of 2 mm. The second radiation detector includes a detecting portion formed of CdTe of a cube having a side of 5 mm. The first radiation detector detects X-rays emitted from an X-ray source and transmitted through an examinee and does not detect γ-rays emitted from the examinee. The second radiation detector detects above X-rays and γ-rays. An X-ray signal processing apparatus processes an X-ray image signal from the first radiation detector and outputs intensity information thereof. A signal discriminating apparatus processes a γ-ray image signal from the second radiation detector and outputs a pulse signal. Thus, the radiological imaging apparatus capable of carrying out radiation examination of the subject by using X-rays and γ-rays can be simplified.

32 Claims, 11 Drawing Sheets

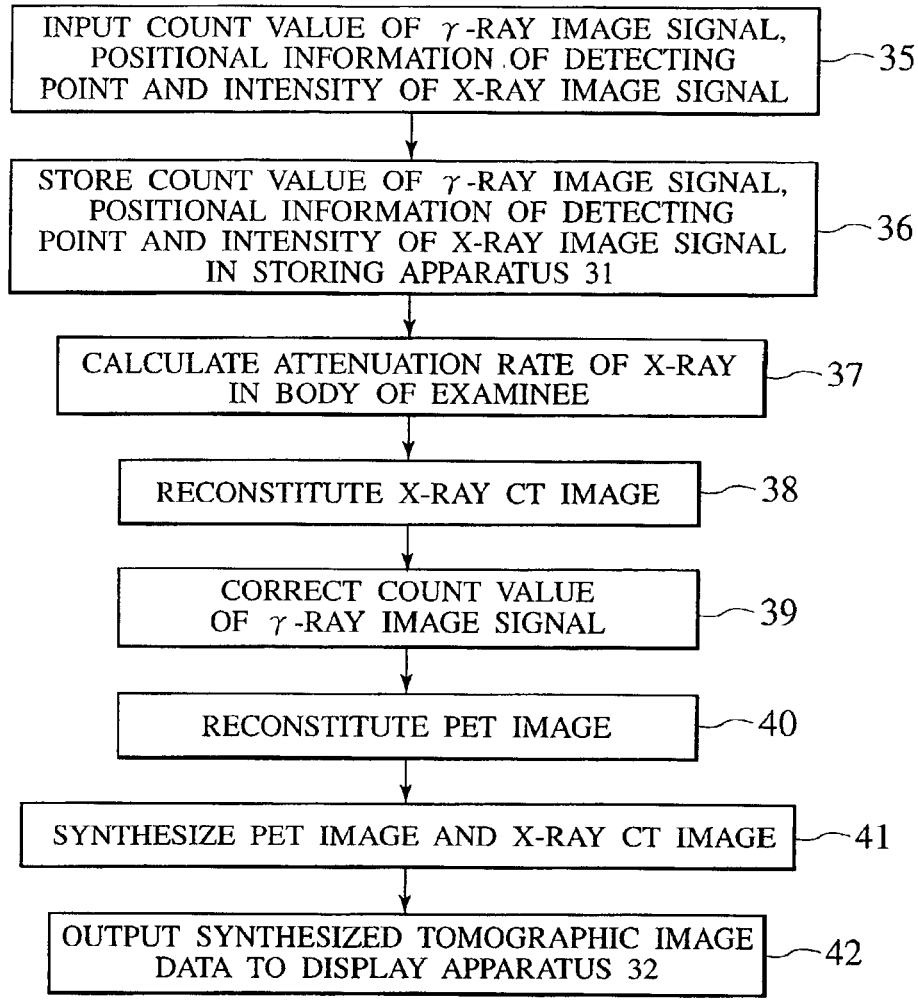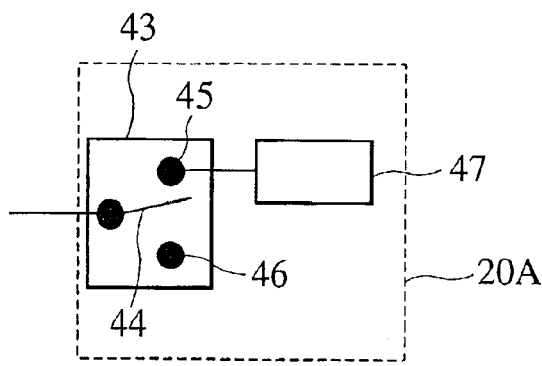

RADIOLOGICAL IMAGING APPARATUS

The present application claims priority to Japanese application No. 2001-393044, filed on Dec. 26, 2001.

BACKGROUND OF THE INVENTION

The present invention relates to a radiological imaging apparatus, and more particularly to a radiological imaging apparatus preferably applicable to X-ray CT, Positron Emission Computed Tomography (hereinafter, referred to as PET), Single Photon Emission Computed Tomography (hereinafter, referred to as SPECT) or the like.

Radiological imaging technology using radiation can examine conformation of a subject non-invasively. In particular, examples of radiological imaging of a human body as a subject include X-ray CT, PET and SPECT. In any of the technologies, by measuring a physical amount of integrated value (flying direction) of radiation radiated from the human body and projecting back the integrated value, the physical amount of each voxel in the human body is calculated and imaged. Enormous data needs to be processed for imaging. Rapid progress of computer technology in recent years enables to provide tomographic images of the human body at high speed with high accuracy.

In X-ray CT, an examinee is irradiated with X-ray from an X-ray source and an intensity of X-ray passing the conformation of the examinee is measured and from a rate of X-ray passing the conformation, mode information on sections of the examinee is imaged, that is, tomographic image of the subject is obtained. More specifically, the intensity of X-ray passing the conformation of the examinee is measured by a radiation detector arranged on a side opposed to the X-ray source relative to the examinee and by using the measured X-ray intensity, a linear attenuation coefficient between the X-ray source and the radiation detector is calculated. Since transmitted X-ray is measured by turning the X-ray source and the radiation detector around the examinee, a distribution of the linear attenuation coefficient in the conformation is calculated. The linear attenuation coefficient of each voxel is calculated by using the Filtered Back Projection Method described in the IEEE Transaction on Nuclear Science NS volume 21, page 21 and the value is converted into a CT value. The radiation source often used in the X-ray CT is around 80 keV.

The PET is a method of administering to the examinee, radio pharmaceuticals (hereinafter, PET pharmaceuticals) containing matters having a property of concentrating on positron emitters ($^{15}O$, $^{12}N$, $^{11}C$, $^{18}F$, etc.) and specific cells in the body and examining locations in the body where more PET pharmaceuticals are consumed. An example of radio pharmaceutical is (2-[F-18] fluoro-2-deoxy-D-flucose, $^{18}FDG$). $^{18}FDG$ is highly concentrated on tumor tissue by carbohydrate metabolism and therefore is used to specify location of tumor. A positron emitted from a positron emitter in the PET pharmaceutical concentrated on a specific location, couples with an electron of a neighboring cell to disappear and irradiates a pair of γ-rays having an energy of 511 keV. These γ-rays are irradiated in directions substantially opposed to each other (180°±0.6°). When the pair of γ-rays is detected by a radiation detector, it is found at which pair of the radiation detectors the positron is emitted. By detecting a number of the pairs of γ-rays a location where the PET pharmaceuticals are more consumed is found. For example, $^{18}FDG$ concentrates on a cancer cell with enhanced carbohydrate metabolism as described above and therefore, cancer focuses can be discovered by PET. Further, the obtained data is converted into a radiation generating density of each voxel by the above-described filtered back projection method to thereby contribute to imaging of a location of generating the γ-ray (a location where radiation radiateters are concentrated on, that is, a location of the cancer cell). $^{15}O$, $^{12}N$, $^{11}C$ and $^{18}F$ used for the PET are radioisotopes having a short half life of 2 to 110 minutes.

According to the examination by PET, data obtained by PET examination is corrected by using the data of a transmission image picked up using a γ-ray source. The transmission image is provided by a method of measuring an attenuation rate of γ-ray in the body by irradiating the γ-ray by using, for example, cesium (γ-ray source) and measuring an intensity of γ-ray passing the body of the examinee. A PET image having high accuracy can be provided by estimating the γ-ray attenuation rate in the body by using the obtained γ-ray attenuation rate and correcting data obtained from the PET.

SPECT administers to the subject, radio pharmaceuticals (hereinafter, referred to as SPECT pharmaceuticals) including single photon radiateters to examine γ-ray radiated from the radiateters by a radiation detector. The energy of γ-ray radiated from single photon radiateters often used in examining by SPECT, is around several 100 keV. In the case of the SPECT, single γ-rays are radiated and therefore, an angle incident on the radiation detector cannot be provided. Hence, angle information is obtained by detecting only γ-ray incident from a specific angle by using a collimator. The SPECT is an examination method which administers to the examinee, SPECT pharmaceuticals containing matters having a property of concentrating on a specific tumor or molecules and single photon radioteters ($^{99}Tc$, $^{67}Ga$, $^{201}Tl$, etc.), detects the γ-rays generated by the SPECT pharmaceutical and specifies a location where the SPECT pharmaceutical is more consumed (for example, a location where a cancer cell is present). The SPECT also converts the obtained data into data of each voxel by the method of filtered back projection or the like. Further, the SPECT also picks up the transmission image frequently. $^{99}Tc$, $^{67}Ga$, $^{201}Tl$ used for the SPECT are provided with a half life longer than that of radioisotopes used in the PET, for example, 6 hours to 3 days.

As described above, the PET and SPECT can sample with good contrast a location where the radio pharmaceutical is integrated since a functioned image is obtained by using metabolism in the body; however, there poses a problem that a positional relationship with surrounding organs cannot be grasped. Hence, in recent years, attention is attracted to a technology of carrying out a diagnosis to a higher degree by synthesizing a mode image which is a tomographic image obtained by X-ray CT and a functioned image which is a tomographic image obtained by PET or SPECT. An example of this technology is described in Japanese Patent Laid-open No. 7-20245.

According to a radiological imaging apparatus described in Japanese Patent Laid-open No. 7-20245, an X-ray CT image pickup apparatus and a PET image pickup apparatus are installed in series and the examinee is examined by using the two image pickup apparatus by moving a bed on which the examinee is laid in the horizontal direction. In this case, a time interval of carrying out the two examinations is short, the examinee hardly moves on the bed and therefore, a corresponding relationship between PET data and X-ray CT data which are imaging data obtained by the two image pickup apparatus is found. By using the corresponding relationship, PET data and X-ray CT data are synthesized and the focus location of the examinee is specified.

Japanese Patent Laid-open No. 9-5441 describes a radiological imaging apparatus serving also as a bed and arranged with an X-ray CT image pickup apparatus and a SPECT image pickup apparatus in series. X-ray CT data and SPECT data which are image pickup data obtained from their respective image pickup apparatus are synthesized and the focus location of the examinee is specified.

Although the radiological imaging apparatus described in the publications are apparently clear in the positional relationship between the two image pickup data, there is a possibility that the examinee constituting the subject is moved between the two image pickup apparatus. Resolution of the PET image pickup apparatus in recent years is about 5 mm and resolution of the X-ray CT image pickup apparatus is about 0.5 mm, smaller than the above-described resolution substantially by one digit. Therefore, when the examinee is moved between the two image pickup apparatus or an angle of the examinee is changed, the corresponding relationship of the respective image pickup data obtained by the two image pickup apparatus become unclear. As a result, after reconstituting images of the respective image pickup data, it is necessary to sample characteristic areas commonly present in the respective images and calculate the positional relationship between the respective images from the positional relationship of the characteristic areas to thereby position the images. Further, the radiological imaging apparatus are provided with two of image pickup apparatus respectively having radiation detectors and the like and therefore, the constitution of the apparatus is complicated.

SUMMARY OF THE INVENTION

It is an object of the invention to provide a radiological imaging apparatus with a simplified apparatus constitution.

The invention for achieving the above-described object is characterized by comprising an image pickup apparatus including a plurality of first radiation detectors, disposed around a hole portion into which a bed is inserted, for not substantially detecting γ-rays from a subject and detecting X-rays and outputting a first detecting signal which is a detecting signal of X-rays, and a second radiation detector, disposed around the hole portion, for detecting γ-rays from the subject and X-rays and outputting both the first detecting signal and a second detecting signal which is a detecting signal of γ-rays, further comprising a first signal processing apparatus for processing the first detecting signal outputted from the first radiation detector, and a second signal processing apparatus for processing the second detecting signal outputted from the second radiation detector.

There are arranged the first radiation detector and the second radiation detector formed in a single piece of an image pickup apparatus around the hole portion to which the subject is inserted and which is shared thereby and therefore, the radiological imaging apparatus capable of carrying out radiation examination of the subject using X-rays and γ-rays can be simplified.

In addition, the invention achieving the above-described object is characterized by comprising an image pickup apparatus including a plurality of first radiation detectors, disposed around a hole portion into which a bed is inserted, for detecting both of γ-rays and X-rays from a subject and outputting both a first detecting signal which is a detecting signal of X-rays and a second detecting signal which is a detecting signal of γ-rays, and a second radiation detector, disposed around the hole portion, for detecting γ-rays and X-rays from the subject and outputting both the first detecting signal and the second detecting signal, further comprising a first signal processing apparatus for processing the first detecting signal outputted from the first radiation detector, and a second signal processing apparatus for processing the second detecting signal outputted from the second radiation detector. The above-described function and effect can be achieved also by the feature.

BRIEF DESCRIPTION OF THE DRAWINGS

Other objects and advantages of the invention will become apparent from the following description of embodiments with reference to the accompanying drawings in which:

FIG. 5 is an explanatory diagram of processing for obtaining a synthesized tomographic image data executed by a computer of FIG. 1;

FIG. 6 is a constitution view of an X-ray signal processing apparatus used in a radiological imaging apparatus of Embodiment 2, which is another embodiment of the invention;

DETAILED DESCRIPTION OF THE PREFERRED EMBODIMENTS (Embodiment 1)

Figure 1:
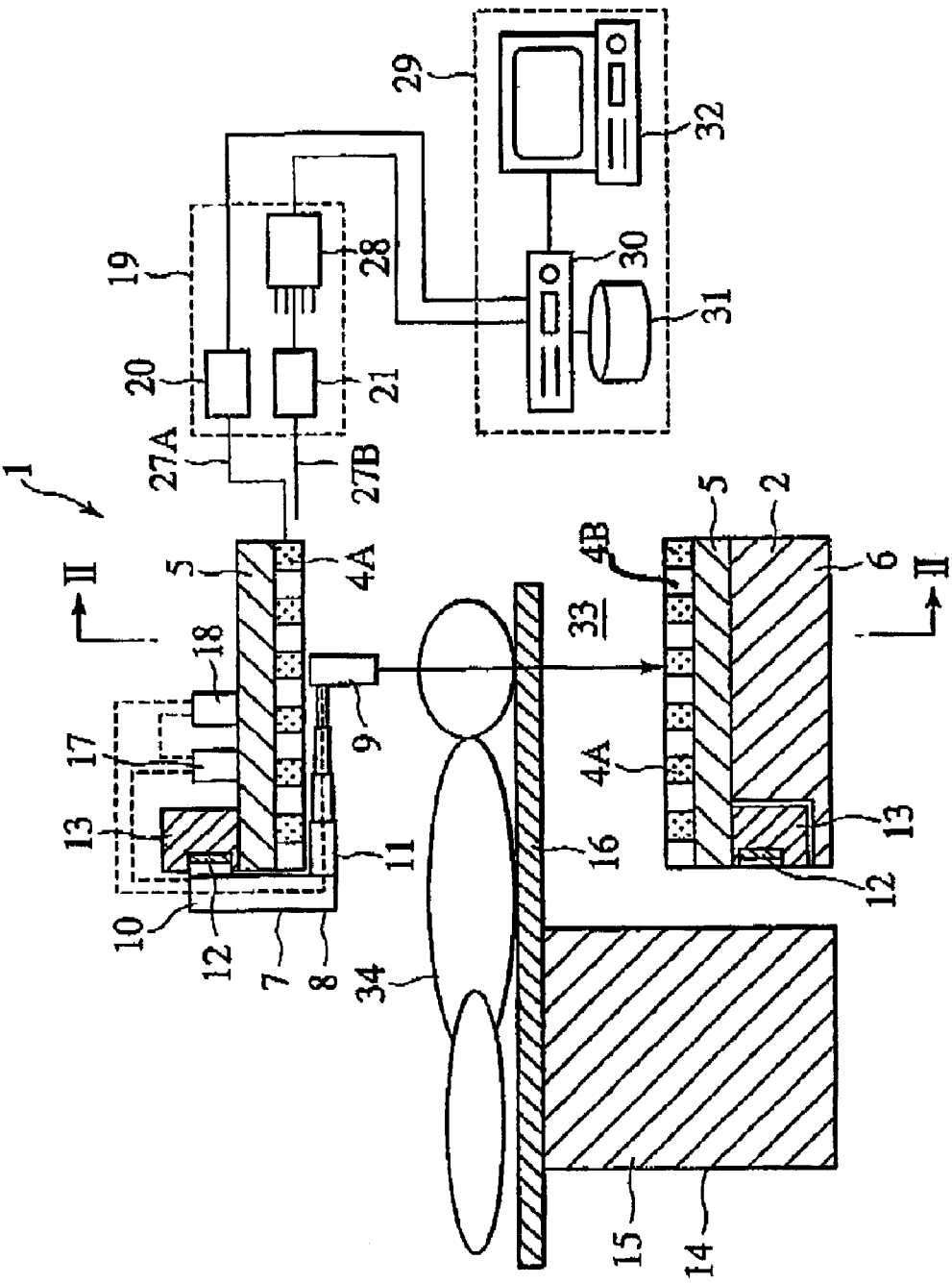
FIG. 1 is a constitution view of a radiological imaging apparatus according to Embodiment 1, which is a preferred embodiment of the invention.
Figure 2:
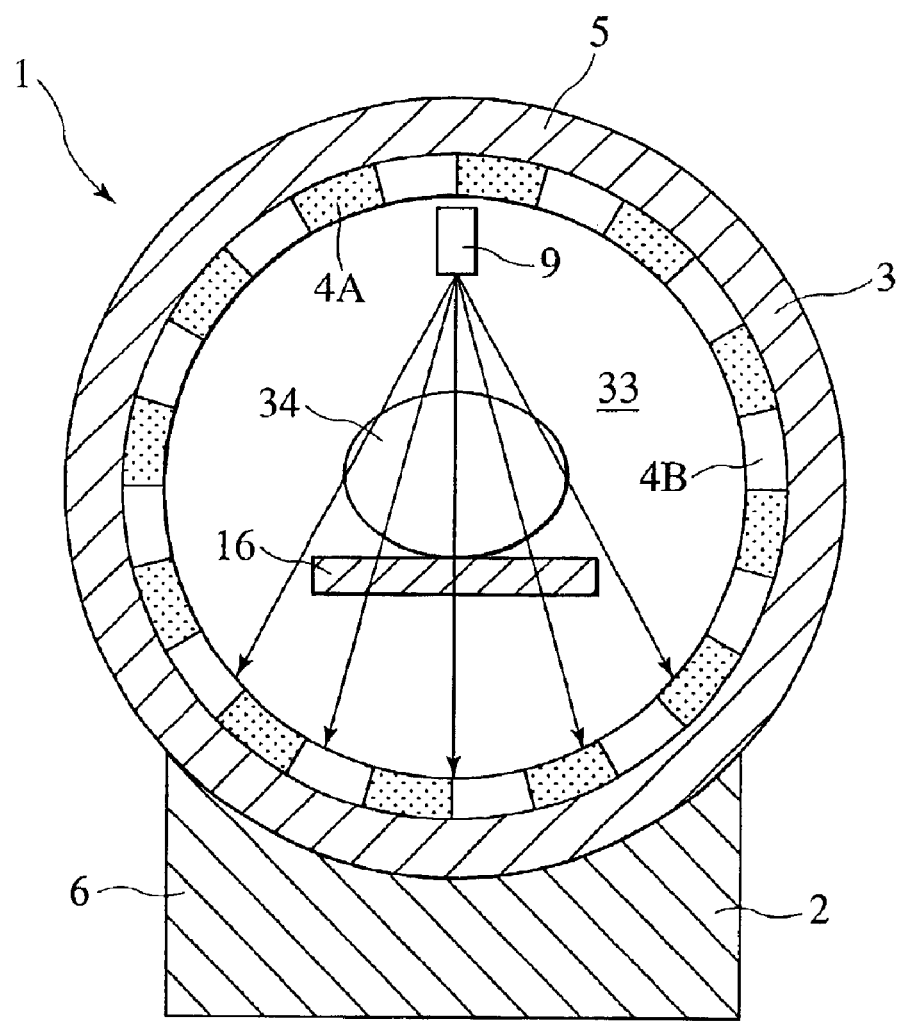
FIG. 2 is a sectional view taken along line II—II of FIG. 1.

A description will be made of a radiological imaging apparatus according to a preferred embodiment of the invention with reference to FIGS. 1 and 2. A radiological imaging apparatus 1 of the embodiment includes an image pickup apparatus 2, an examinee holding apparatus 14, a signal processing apparatus 19 and a tomographic image forming apparatus 29. The examinee holding apparatus 14 has a support member 15, and a bed 16 disposed at an upper end portion of the support member 15 and movable in the longitudinal direction.

Figure 3:
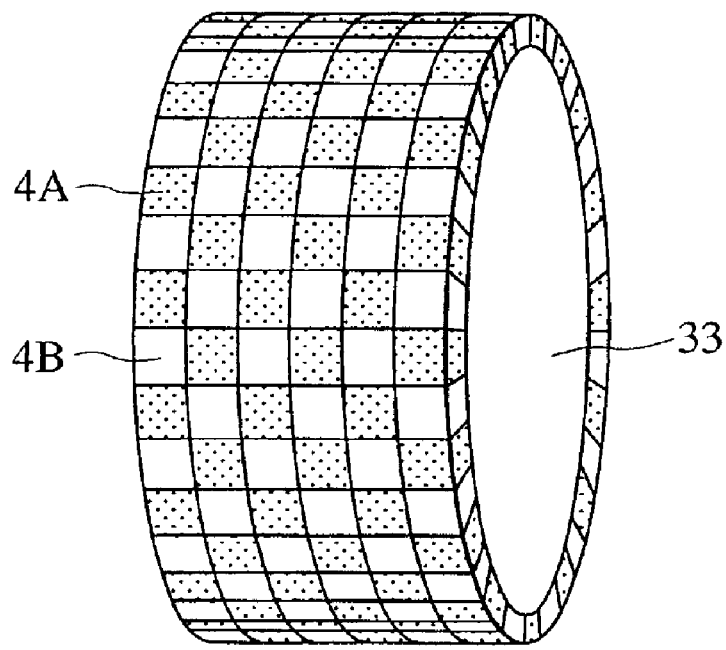
FIG. 3 is a perspective view showing an alignment of radiation detectors in a group of circular radiation detectors of FIG. 1.

The image pickup apparatus 2 is installed in a direction orthogonal to the longitudinal direction of the bed 16 and includes radiation detectors 4A and 4B, an X-ray source circumferential direction moving apparatus 7, a drive controller 17 and an X-ray source control apparatus 18. A support member 6 is installed inside a casing (not illustrated) of the image pickup apparatus 2. The radiation detectors 4A and 4B are installed on a circular holder 5 supported by the support member 6 and disposed inside the casing. The radiation detectors are disposed circularly in such a manner as to surround a hole portion 33 formed in the casing. A plurality of rows of the radiation detectors (10000 in total) is installed in the axial direction of the hole portion 33. That is, pluralities of the radiation detectors 4A and 4B constitute a group of circular radiation detectors surrounding the hole portion 33 and extending in the axial direction of the hole portion 33. The radiation detectors 4A and 4B are semiconductor radiation detectors. The radiation detector 4A includes a detecting portion in square having a side of 5 mm and a thickness of 1 mm, formed of gallium arsenide. The radiation detector 4B includes a detecting portion in cube having a side of 5 mm, formed of cadmium telluride. The detecting portion of the radiation detector 4B may be a cube having a side of 5 mm, formed of GaAs or cadmium zinc telluride (CZT). As schematically shown by FIG. 3, the radiation detectors 4A and 4B are alternately disposed in the circumferential direction and the axial direction of the hole portion 33. Therefore, the respective row of the circular radiation detectors disposed in the axial direction of the hole portion 33 includes the radiation detectors 4A and 4B. The drive controller 17 and the X-ray source control apparatus 18 are installed at an outer face of the circular holding portion 5 in the casing. The examinee holding apparatus 14 may be connected to the casing (not illustrated) of the image pickup apparatus 2.

The radiation detector 4A has sensitivity of detecting γ-ray of 511 keV lower than that of X-ray of 80 keV since the detecting portion is formed of GaAs having a small atomic mass number and is as thin as 1 mm in thickness. In other words, even if γ-ray having energy higher than that of X-ray enters the radiation detector 4A, the γ-ray is not detected by the radiation detector 4A and passes the detecting portion of the radiation detector 4A without being detected. Thus, the radiation detector 4A selectively detects X-ray. The γ-ray is detected by the radiation detector 4B. Even the detecting portion formed of GaAs can detect the γ-ray if it is 5 mm in thickness.

The X-ray source peripheral direction moving apparatus 7 is provided with an X-ray source apparatus 8 and a circular X-ray source apparatus-holding portion 13. The X-ray source holding portion 13 is attached to an outer face of the circular holding portion 5 at one end thereof. A circular guide rail 12 is installed at one end face of the X-ray source apparatus-holding portion 13. The guide rail 12 and the X-ray apparatus holding portion 13 surround the hole portion 33. The X-ray source apparatus 8 includes an X-ray source 9, an X-ray source driving apparatus 10 and an axial direction moving arm 11. The X-ray source drive apparatus 10 is provided with a first motor and a power transmitting mechanism having a speed reduction mechanism in a drive source casing, although not illustrated. The power transmitting mechanism is coupled to a rotary shaft of the first motor. The axial direction moving arm 11 is attached to the drive apparatus casing and extends in the hole portion 33. The X-ray source 9 is attached to the axial direction moving arm 11. The axial direction moving arm 11 is extracted and contracted in the axial direction of the hole portion 33 and moves the X-ray source 9 in the axial direction of the hole portion 33. The axial direction moving arm 11 is extracted and contracted by operating a second motor (not illustrated) installed at the X-ray source drive apparatus 10. The X-ray source drive apparatus 10 is mounted to the guide rail 12 so as not to be dropped and movably along the guide rail 12. The X-ray source drive apparatus 10 includes a pinion for receiving rotational force from the power transmitting mechanism, although not illustrated. The pinion is brought in mesh with a rack provided at the guide rail 12.

The X-ray source 9 includes a publicly known X-ray tube, although not illustrated. The X-ray tube is provided with an anode, a cathode, a current source of the cathode and a voltage source for applying voltage between the anode and the cathode. The cathode is a filament made of tungsten. Electrons are emitted from the filament by allowing current to flow from the current source to the cathode. The electron is accelerated by a voltage (80 kV) applied between the cathode and the anode from the voltage source and impacts against the anode (W, Mo or the like) as a target. The impact of electron to the anode causes a maximum of 80 keV of X-ray. The X-ray is irradiated from the X-ray source 9.

Figure 4:
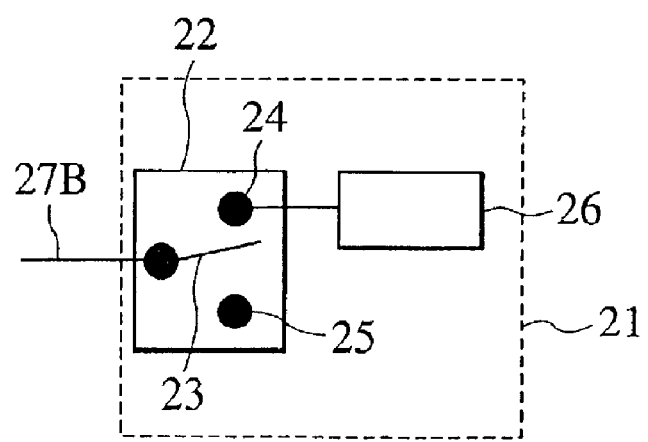
FIG. 4 is a detailed constitution view of a signal discriminating apparatus shown in FIG. 1.

The signal processing apparatus 19 is provided with an X-ray signal processing apparatus 20, a signal discriminating apparatus 21 and a simultaneous counting apparatus 28. The X-ray signal processing apparatus 20 is provided for each radiation detector 4A and is connected to the associated radiation detector 4A by a wiring 27A. The signal discriminating apparatus 21 is provided for each radiation detector 4B and is connected to the associated radiation detector 4B by a wiring 27B. As shown in FIG. 4, the signal discriminating apparatus 21 includes a changeover switch 22 and a γ-ray discriminating apparatus 26. The changeover switch 22 includes a movable terminal 23 and fixed terminals 24 and 25. The wiring 27B is connected to the movable terminal 23 and the γ-ray discriminating apparatus 26 is connected to the fixed terminal 24. The fixed terminal 25 is only brought into contact with the movable terminal 23 through switching. The γ-ray discriminating apparatus 26 of the respective signal discriminating apparatus 21 is connected to the single simultaneous counting apparatus 28. The simultaneous counting apparatus 28 may be provided for each of several γ-ray discriminating apparatus 26. The tomographic image forming apparatus 29 includes a computer 30, a storing apparatus 31 and a display apparatus 32. The computer 30 is connected to the respective X-ray signal processing apparatus 20 and the simultaneous counting apparatus 28. The storing apparatus 31 and the display apparatus 32 are connected to the computer 30.

The embodiment is an example of carrying out X-ray CT examination (action of detecting X-rays radiated from the X-ray source 9 and transmitted through the body of the examinee using the radiation detector) as well as PET examination (action of detecting γ-rays radiated from the body of the examinee caused by the PET pharmaceutical using the radiation detector) by using a single piece of the image pickup apparatus 2.

Before carrying out radiation examination, first, an examinee 34 who is the subject, is administered with the PET pharmaceutical previously by a method of injection or the like so that radioactivity administered to the body becomes 370 MBq. The PET pharmaceutical is selected in accordance with an object of examination (grasping location of cancer or examination of an aneurism of heart). The examinee 34 is at standby during a predetermined time period until the PET pharmaceutical is diffused in the body and concentrated on an affected portion in a state of being able to pick up an image thereof. Elapse of the predetermined time period causes the PET pharmaceutical to concentrate at an affected portion (for example, affected portion of cancer) of the examinee 34. After elapse of the predetermined time of period, the examinee 34 is laid on the bed 16 of the examinee holding apparatus 14. The X-ray CT examination and PET examination according to the embodiment are carried out by using the image pickup apparatus 2 in a state in which the examinee 34 is inserted into the hole portion 33 by moving the bed 16 on which the examinee 34 administered with the PET pharmaceutical is laid.

The X-ray source control apparatus 18 controls a time period of emission of X-rays from the X-ray source 9. To be more specific, during X-ray CT examination, the X-ray source control apparatus 18 repeats control of closing a switch (hereinafter, referred to as X-ray source switch, not illustrated) provided between the anode (or cathode) of the X-ray tube in the X-ray source 9 and a power source by outputting an X-ray generating signal, opening the X-ray source switch by outputting an X-ray stopping signal after elapse of a first set time period, and closing the X-ray source switch after elapse of a second set time period. Voltage is applied between the anode and the cathode during the first set time period and voltage is not applied during the second set time period. This control allows X-rays to be emitted from the X-ray tube in a pulse-like manner. An irradiation time period T, which is the first set time period, is set to, for example 1 μsec. This 1 μsec corresponds to a time period while γ-rays are not detected in the radiation detector 4B (a time period while a probability of detecting γ-rays in the radiation detector 4 for detecting X-ray described in Embodiment 2 can be disregarded). The second set time period is a time period T0 while the X-ray source 9 is moved from one radiation detector to another radiation detector contiguous thereto in the circumferential direction and is determined by moving speed of the X-ray source 9 in the circumferential direction of the guide rail 12. The first and the second set time periods are stored in the X-ray source control apparatus.

When the X-ray CT examination is started, the drive controller 17 issues a drive start signal to close a switch (hereinafter, referred to as first motor switch) connected to the first motor of the X-ray source drive apparatus 10 and connected to the power source. Supply of a current rotates the first motor and the rotational force is transmitted to the pinion via the power transmitting mechanism. Since the pinion in mesh with the rack of the guide rail 12 is rotated, the X-ray source apparatus 8, that is, the X-ray source 9 is moved in the circumferential direction along the guide rail 12. The X-ray source 9 is moved at set speed around the examinee 34 in a state of being inserted into the hole portion 33. When the X-ray CT examination is finished, the drive controller 17 opens the first motor switch by outputting a drive stop signal. This stops movement of the X-ray source 9 in the circumferential direction is stopped. With this embodiment, all the radiation detectors 4A and 4B are not moved in the peripheral direction of the hole portion 33 and are not moved also in the axial direction of the hole portion 33. The publicly known technology which does not hamper movement of the X-ray source apparatus 10 is applied to transmission of control signals to the moving X-ray source apparatus 10 from the unmoved X-ray source control apparatus 18 and the unmoved drive controller 17.

The X-ray source control apparatus 18 receives the drive start signal outputted from the drive controller 17 when the X-ray CT examination is started. The X-ray source control apparatus 18 outputs an X-ray generating signal based on reception of the drive start signal. Thereafter, The X-ray source control apparatus 18 repeatedly outputs the X-ray stopping signal and the X-ray generating signal. By the repeated output of the X-ray stopping signal and the X-ray generating signal, the X-ray source 9 emits X-rays during the first set time period, that is, 1 μsec and stops emission of X-rays during the second set time period. The emission and stop of X-rays are repeated during a time period of moving the X-ray source 9 in the circumferential direction. The X-rays radiated from the X-ray source 9 are irradiated to the examinee 34 inserted into the hole portion 33 in a fan beam manner. By movement of the X-ray source 9 in the circumferential direction, the examinee 34 on the bed 16 is irradiated with X-rays from the surrounding thereof. The X-rays are have a certain width in the circumferential direction of the guide rail 12 and therefore, after transmitting the examinee 34, the X-rays are detected by the plurality of radiation detectors 4A and 4B disposed in the circumferential direction centering on the radiation detector disposed at a position 180 degrees from the X-ray source 9 with an axial center of the hole portion 33 as a base point. The radiation detectors 4A and 4B output detecting signals of the X-rays (hereinafter, referred to as X-ray image signal). At this occasion, the radiation detector 4B does not detect γ-rays. The X-ray image signal from the radiation detector 4A enters a corresponding one of the X-ray signal processing apparatus 20 via a corresponding one of the wiring 27A. The X-ray image signal from the radiation detector 4B enters a corresponding one of the signal discriminating apparatus 21 via a corresponding one of the wiring 27B. When X-rays are radiated from the X-ray source 9, the radiation detectors 4A and 4B disposed at an area the X-rays enter (X-ray-incident-area) are referred to as first radiation detectors for convenience. The radiation detectors 4A and 4B disposed outside the X-ray incident area are referred to as second radiation detectors for convenience. Each of the radiation detectors 4A and 4B installed at the circular holding portion 5, becomes the first radiation detector in one case and become the second radiation detector in other case in view of a relationship with the position of the X-ray source 9.

γ-rays of 511 keV caused by PET pharmaceutical is emitted from the examinee 34 on the bed 16 inserted into the hole portion 33. The radiation detector 4B included in the second radiation detector does not detect X-rays but detects γ-rays emitted from the examinee 34 and outputs a detected signal of the γ-rays (hereinafter, referred to as γ-ray image signal). The γ-ray image signal enters a corresponding one of the signal discriminating apparatus 21 via a corresponding one of the wiring 27B. The radiation detector 4A included in the second radiation detector does not detect γ-rays caused by the PET pharmaceutical.

The X-ray signal processing apparatus 20 that received the X-ray image signal from the radiation detector 4A of the first radiation detector outputs a current value of the X-ray image signal, that is, information on intensity of the X-ray image signal by processing the X-ray image signal by a differential circuit. The X-ray CT examination is carried out in the axial direction of the body of the examinee 34 by extending (or contracting) the axial direction move arm 11. The bed 16 may be moved in the axial direction of the hole portion 33 as necessary.

An explanation will be given of processing of the signal outputted from the radiation detector 4B in the signal discriminating apparatus 21. The changeover switch 22 carries out switching operation for connecting the movable terminal 23 to either of the fixed terminals 24 and 25. Such switching operation of the movable terminal 24 is carried out based on a switch control signal, which is an output of the drive controller 17. The drive controller 17 selects the radiation detector 4B included in the first radiation detector and connects the movable terminal 23 of the changeover switch 22 in the signal discriminating apparatus 21 connected to the selected radiation detector 4B to the fixed terminal 25. A time period while the movable terminal 23 is connected to the fixed terminal 25 is a time period of the first set time period while X-rays are emitted from the X-ray source 9 (1 μsec in the embodiment). Therefore, the X-ray image signal from the radiation detector 4B is not inputted to the γ-ray discriminating apparatus 26 of the signal discriminating apparatus 21. Further, when the radiation detector 4B becomes the second radiation detector, the drive controller 17 connects the movable terminal 23 to the fixed terminal 24. Therefore, the γ-ray image signal from the radiation detector 4B enters the γ-ray discriminating apparatus 26.

A simple explanation will be given of selection of the first radiation detector. The first motor in the X-ray source drive apparatus 10 is connected with an encoder (not illustrated). The drive controller 17 receives a detecting signal of the encoder, calculates a position of the X-ray source drive apparatus 10, that is, the X-ray source 9 in the circumferential direction and selects the radiation detectors 4A and 4B disposed in the X-ray incident area centering on a position on a side opposed to the position of the X-ray source 9 by 180° by using data storing positions of the plurality of respective radiation detectors. Also the first radiation detector seems as if the first radiation detector were spuriously moved in the circumferential direction in accordance with movement of the X-ray source 9. The drive controller 17 connects the movable terminal 23 connected to the radiation detector 4B newly constituting the first radiation detector to the fixed terminal 25 and connects the movable terminal 23 connected to the radiation detector 4B which is not the first radiation detector, to the fixed terminal 24.

The γ-ray discriminating apparatus 26 does not receive an output signal of the radiation detector 4B when the radiation detector 4B is the first radiation detector and receives the γ-ray image signal from the radiation detector 4B when the radiation detector 4B becomes the second radiation detector. An explanation will be given of processing the γ-ray image signal. The γ-ray image signal is converted into a γ-ray image signal having a waveform of a temporal Gaussian distribution in a waveform-shaping portion (not illustrated) of the γ-ray discriminating apparatus 26. A filter unit (not illustrated) of the γ-ray discriminating apparatus 26 permits the γ-ray image signal having energy equal to or larger than an energy set value (for example, 450 keV) in the γ-ray image signal the waveform of which has been converted to pass therethrough and hampers the γ-ray image signal having energy less than the energy set value from passing therethrough. That is, the γ-ray discriminating apparatus 26 generates a pulse signal having predetermined energy with respect to the γ-ray image signal passing the filter unit, that is, the γ-ray image signal having energy equal to or larger than the energy set value. The γ-ray discriminating apparatus 26 is an apparatus of generating the pulse signal with respect to the γ-ray image signal of predetermined energy.

The signal discriminating apparatus 21 is a γ-ray image signal processing apparatus for selectively processing the γ-ray image signal. The γ-ray image signal processing apparatus is provided with the changeover switch 22 which is a γ-ray image signal selecting apparatus controlled by the drive controller 17 so as to select the γ-ray image signal and the γ-ray discriminating apparatus 26 which is the pulse signal generating apparatus for outputting the pulse signal by processing the γ-ray image signal selected by the γ-ray image signal selecting apparatus.

The simultaneous counting apparatus 28 receives the pulse signal from the γ-ray discriminating apparatus 26 of the respective signal discriminating apparatus 21, perform simultaneous counting, and using the pulse signal, calculates a count value with respect to the γ-ray image signal. Further, the simultaneous counting apparatus 28 calculates positions of two detecting points detecting the above-described pair of γ-rays by a pair of the pulse signals with respect to the pair of γ-rays (positions of a pair of the radiation detectors having directions different from each other substantially by 180° (strictly 180°±0.6°)). According to the embodiment, the radiation detectors 4B are respectively arranged on sides opposed to each other by 180° centering on the axial center of the hole portion 33.

The computer 30 executes processing based on a processing procedure of steps 35 through 42 shown in FIG. 5. The computer 30 receives the count value of the γ-ray image signal and the positional information on the detecting point outputted from the simultaneous counting apparatus 28 and intensity of the X-ray image signal outputted from the respective X-ray signal processing apparatus 20 (step 35). The storing apparatus 31 stores the received count value of the γ-ray image signal, the received positional information on the detecting point and the received intensity of the X-ray image signal (step 36). By using the intensity of the X-ray image signal stored in the storing apparatus 31, an attenuation rate of X-ray in each voxel in the body of the examinee 34 is calculated (step 37). The attenuation rate is stored in the storing apparatus 31.

Tomographic images of cross-sectional faces of the examinee 34 are reconstituted by using the attenuation rates of the X-ray image signals at corresponding positions (step 38). The tomographic images reconstituted by using the attenuation rates of the X-ray image signals are referred to as X-ray CT images, the tomographic images including images of internal organs and bones of the examinee 34. In order to reconstitute the X-ray CT images, by using the attenuation rates of the X-ray image signals read from the storing apparatus 31, linear attenuation coefficients in the body of the examinee 34 between the X-ray source 9 and semiconductor detecting portions of the radiation detectors 4A detecting X-ray are calculated. By using the linear attenuation coefficients, linear attenuation coefficients of the respective voxels are calculated by the filtered back projection method. CT values of the respective voxels are provided by using values of the linear attenuation coefficients of the respective voxels. By using the CT values, data of the X-ray CT images is provided. The data of the X-ray CT images is stored in the storing apparatus 31.

γ-rays generated at the an affected portion are absorbed and attenuated while transmitting the body and therefore, it is also possible to provide count values of the γ-ray image signals with higher accuracy by estimating the effects from data of the attenuation rates noted above and correcting the count values of the γ-ray image signals. At step 39, the count values of the γ-ray image signals are corrected. A description will be made of an example of a correcting method with regard to the count values of the γ-ray image signals below. First, the tomographic images of the examinee 34 are reconstituted by using the attenuation rates of the X-ray image signals and CT values at the respective positions in the body are calculated. From the provided CT values, substance compositions at the respective positions are estimated. Further, from the substance composition data, the linear attenuation coefficients at the respective positions at 511 keV are estimated. By using the provided linear attenuation coefficient data of the respective voxels, the linear attenuation coefficients between pairs of semiconductor element portions detecting the pairs of γ-rays are obtained by the forward projection method. By multiplying the count values of the γ-ray image signals by inverse numbers of the calculated linear attenuation coefficients, differences of data due to attenuation in the body are corrected.

Tomographic images of the cross-sectional faces of the examinee 34 including the affected portion (for example, affected portion of cancer), are reconstituted by using the corrected count values of the γ-ray image signals at corresponding positions (step 40). The tomographic images reconstituted by using the count values of the γ-ray image signals are referred to as PET images. A detailed explanation will be given of the processing. By using the count values of the γ-ray image signals read from the storing apparatus 31, calculated are numbers of generating γ-ray pairs (number of γ-ray pairs generated in accordance with disappearance of a plurality of positrons) in the body between the respective semiconductor detecting portions of pairs of the radiation detectors 4B detecting γ-rays generated caused by disappearance of positrons (specified by the positional information on the detecting points). By using the γ-ray pair generating numbers, densities of γ-ray pairs generating at the respective voxels are calculated by the filtered back projection method. Based on the γ-ray pair generating densities, data of PET images can be provided. The data of the PET images are stored in the storing apparatus 31.

By synthesizing data of the PET images and data of the X-ray CT images, synthesized tomographic images including the two data are calculated and stored in the storing apparatus 31 (step 41). Data of the PET images and data of the X-ray CT images can simply, accurately be synthesized by aligning positions of central axes of the hole portion 33 in the two image data. That is, data of the PET images and data of the X-ray CT images are formed based on the image signals outputted from the radiation detectors 4A and 4B included in rows of the circular radiation detectors inside the single image pickup apparatus 2 and therefore, positioning can accurately be carried out as mentioned above. Data of the synthesized tomographic images is called up from the storing apparatus 31, outputted to the display apparatus 32 (step 42) and displayed on the display apparatus 32. The synthesized tomographic images displayed on the display apparatus 32 include the X-ray CT images and therefore, a position of an affected portion in the PET images in the body of the examinee 34 can easily be confirmed. That is, the X-ray CT images include images of internal organs and bones and therefore, doctors can specify the position where the affected portion (for example, an affected portion of cancer) is present by its relationship with the internal organs and the bones.

Further, a plurality of scanning data are needed for the X-ray CT images and in order to obtain a single two-dimensional section data, the X-ray source 9 is moved along the guide rail 12 by using the X-ray source drive apparatus 10 and a necessary amount of data is obtained by the radiation detectors 4. By scanning the X-ray source 9 in the conferential direction in this way, the embodiment provides the two-dimensional section data with regard to the X-ray image signals in the single cross-sectional face of the examinee 34 is obtained. Two-dimensional section data with regard to the X-ray image signals in other cross-sectional faces can be provided by moving the X-ray source 9 in the axial direction of the hole portion 33 by extending and contracting the axial direction moving arm 11. Piling up the two-dimensional section data can provide three-dimensional section data. By using the three-dimensional section data, data of three-dimensional X-ray CT images can be obtained. Helical scanning of X-rays can also be carried out by continuously extending and contracting the axial direction moving arm 11 in the axial direction of the hole portion 33 in accordance with turning of the X-ray source 9. The two dimensional section data with regard to the X-ray image signals in other cross-sectional face can be provided also by moving the bed 16 in the axial direction of the hole portion 33 instead of extending and contracting the axial direction moving arm 11.

According to the embodiment, the following effects can be achieved.

(1) According to the embodiment, the radiation detectors 4B arranged circularly can detect pluralities of pairs of γ-rays emitted from the examinee 34 who is the subject and the radiation detectors 4A arranged circularly also X-rays emitted from the X-ray source 9 moving in the circumferential direction and transmitted through the examinee 34. Therefore, although according to the prior art, as the image pickup apparatus, the image pickup apparatus for detecting transmitted X-rays as well as another image pickup apparatus for detecting γ-rays are needed, according to the embodiment, there may be provided only a single piece of the image pickup apparatus having the radiation detectors 4A and 4B and a constitution of the radiation examining apparatus capable of carrying out both the X-ray CT examination and the PET examination can be simplified. Incidentally, a length of the rows of the radiation detectors in the axial direction of the hole portion 33 of the embodiment is the same as that of the image pickup apparatus for PET of the prior art.

(2) According to the embodiment, the rows of the circular radiation detectors include the radiation detectors 4A that do not detect γ-rays and therefore, a constitution of the processing apparatus of the X-ray image signals connected to the radiation detectors 4A can be simplified. Such a constitution also contributes to further simplification of the constitution of the radiological imaging apparatus and downsizing the radiological imaging apparatus.

(3) The embodiment can reconstitute the first tomographic images (X-ray CT images) including images of internal organs and bones of the examinee 34 by using the X-ray image signals which are output signals of the radiation detectors 4A included in the rows of the circular radiation detectors, further, can reconstitute the second tomographic images (PET image) including the image of the affected portion of the examinee 34 by using the γ-ray image signals which are output signals of the radiation detectors 4B included in the rows of the radiation detectors. Data of the first tomographic images and data of the second tomographic images are reconstituted based on output signals of the radiation detectors 4A and 4B arranged at the surrounding of the hole portion 33 sharing the axis core and therefore, data of the first tomographic images and data of the second tomographic images can be synthesized by accurately positioning the data. Therefore, the tomographic images (synthesized tomographic images) including images of the affected portion, internal organs and bones can simply be provided with excellent accuracy. According to the synthesized tomographic images, the position of the affected portion can accurately be known in the relationship with the internal organs and bones. For example, by combining data of the first tomographic images and data of the second tomographic images by centering on the axial center of the hole portion 33 shared by the respective tomographic image data, the image data synthesized with the two tomographic images can simply be obtained.

(4) According to the embodiment, the image signals necessary for forming the first tomographic images and the image signals necessary for forming the second tomographic images can be obtained from the radiation detectors 4A and 4B arranged around the single hole portion 33 and therefore, a time period required for the examination of the examinee 34 (examination time period) can significantly be shortened. In other words, in the short examination time period, the imaging signals necessary for forming the first tomographic images and the imaging signals necessary for forming the second tomographic images can be provided. According to the embodiment, it is not necessary to move the examinee from the image pickup apparatus for detecting transmitted X-rays to another image pickup apparatus for detecting γ-rays as in the prior art and a probability of movement of the examinee can be reduced. The fact that it is not necessary to move the examinee from the image pickup apparatus for detecting transmitted X-rays to another image pickup apparatus for detecting γ-rays contributes to shortening of the time period of examination of the examinee 34.

(5) According to the embodiment, the radiation detectors 4A and 4B are not moved in the circumferential direction and the axial direction of the hole portion 33 by turning the X-ray source 9 and therefore, a capacity of a motor for turning the X-ray source 9 can be made smaller than that of a motor necessary for moving the circular holding portion 5 installed with the radiation detectors 4A and 4B. Power consumption required for driving the motor of the X-ray source 9 can be made smaller than that of the motor of the circular holding portion 5.

(6) According to the embodiment, the semiconductor radiation detectors are used as the radiation detectors 4A and 4B and therefore, the image pickup apparatus 2 can significantly be made compact.

(7) According to the embodiment, the γ-ray image signals are not included in the signals inputted to the X-ray signal processing apparatus, further, the X-ray image signals are not included in the signals inputted to the γ-ray discriminating apparatus and therefore, data of the X-ray CT images and data of the PET images can be provided with excellent accuracy. Thus, by using the synthesized tomographic image data, the position of the affected portion can further accurately be found.

(8) According to the embodiment, the X-ray source 9 is turned on the inner sides of the radiation detectors 4A and 4B arranged circularly and therefore, the diameter of the circular holding portion 5 is increased and the number of the respective radiation detectors capable of being installed in the circumferential direction on the inner side of the circular holding portion 5 can be increased. An increase in the number of radiation detectors in the circumferential direction enhances the sensitivity and enhances the resolution of the cross-sectional faces of the examinee 34.

(9) According to the embodiment, the axial direction moving arm 11 attached to the X-ray source 9 and the X-ray source 9 are disposed on the inner sides of the radiation detectors 4A and 4B and therefore, there is a possibility that the axial direction moving arm 11 and the X-ray source 9 block γ-rays emitted from the examinee 34, the radiation detector disposed right behind them cannot detect the γ-ray and detected data necessary for forming the PET image becomes deficient. However, according to the embodiment, as described above, the X-ray source 9 and the axial direction moving arm 11 are turned in the circumferential direction by the X-ray source drive apparatus 10 and therefore, the deficiency of data does not substantially pose a problem. In particular, the turning speed of the X-ray source 9 and the axial direction moving arm 11 is about 1 second/1 slice and the time of turning is sufficiently shorter than a time period required for the PET examination which is in the order of several minutes at the shortest, also whereby, the deficiency of the data does not substantially pose the problem. Further, when the X-ray CT examination is not carried out, apparatus related to the X-ray CT examination are constituted such that it is removed from the inside of the radiation detector 4 and stored. For example, according to the embodiment, the X-ray source 9 is constituted such that it is stored in the X-ray source drive apparatus 10.

Further, the examination time period required for obtaining the X-ray image signals necessary for forming the X-ray CT images is shorter than the examination time period required for obtaining the γ-ray image signals necessary for forming the PET images. Therefore, during the examination time period for obtaining the γ-ray image signals, by providing the X-ray image signals by irradiating X-rays to the examinee always from the X-ray source 3, even when the examinee is moved in the examination, from continuous images of the X-ray CT images provided based on the X-ray image signals, deviation of data of the PET images accompanied by rocking of the examinee can also be corrected.

Although according to the embodiment, all the rows of the radiation detectors disposed in the axial direction of the hole portion 33 are constituted to include the radiation detectors 4A and 4B, there may be constructed a constitution in which part of the rows of the radiation detectors includes the radiation detectors 4A and 4B and remaining rows of the radiation detectors do not include the radiation detectors 4A but include the radiation detectors 4B.

(Embodiment 2)

A description will be made of a radiological imaging apparatus, which is another embodiment of the invention. According to the radiological imaging apparatus of the embodiment, the radiation detector 4A in Embodiment 1 is replaced by a radiation detector 4C having a detecting portion constituted by cadmium telluride (CdTe) of a cube having a side of 5 mm. As shown by FIG. 6, the radiation detector 4C is connected to an X-ray signal processing apparatus 20A by the wiring 27A. The radiation detectors 4B and 4C are alternately arranged in the circumferential direction and the axial direction of the hole portion 33 similar to arrangement of the radiation detectors 4A and 4B in FIG. 3. As shown by FIG. 6, the X-ray signal processing apparatus 20A includes a changeover switch 43 and an X-ray intensity calculating apparatus 47. The changeover switch 43 includes a movable terminal 44 and fixed terminals 45 and 46. The movable terminal 44 is connected to the radiation detector 4C by the wiring 27A. The X-ray intensity calculating apparatus 47 is connected to the fixed terminal 45. The X-ray signal processing apparatus 20A is provided for each radiation detector 4C. The other constitutions of the radiological image pickup apparatus according to the embodiment are similar to the radiological imaging apparatus 1 of Embodiment 1.

An explanation will be given of a principle of detecting X-ray transmitted through the examinee 34 according to the embodiment. The embodiment has been carried out based on the following investigation by the inventors. Data of X-ray CT images is formed by repeating operations (scanning) of irradiating the examinee with X-rays irradiated from the X-ray source in a specific direction during a predetermined time period and detecting X-rays transmitted through the body and based on intensity of X-rays detected by a plurality of the radiation detectors. In order to obtain data of the X-ray CT images with excellent accuracy, it is preferred that in the X-ray CT examination γ-rays emitted from the conformation of the examinee caused by the PET pharmaceutical do not enter the X-ray detector that is detecting X-rays. For this purpose, a time period of irradiating the examinee with X-rays is shortened based on new knowledge of the inventors "in one radiation detector, when a time period of irradiating X-rays to an examinee in correspondence with a rate of incidence of γ-rays is shortened, influence of γ-rays is negligible". In order to determine the irradiation time period T of X-rays, first, a consideration is given to the rate of incidence of γ-rays to one radiation detector. When radioactivity in the body based on the PET pharmaceutical administered to the examinee in the PET examination, is designated by notation N (Bq), a rate of passing generated γ-ray in the body is designated by notation A, a rate of incidence calculated from a solid angle of one radiation detector is designated by notation B and a sensitivity of a detection element is designated by notation C, a rate a (count/sec) of γ-rays detected by one radiation detector is given by Equation (1). In Equation (1), a coefficient of "2" signifies that a pair "2 piece" of γ-rays are irradiated when one piece of positron disappears.

$$\alpha = 2NABC \quad (1)$$

A probability W for detecting γ-rays by one detection element during the irradiation time period T is given by Equation (2). By determining the radiation time period T such that a value of W in Equation (2) is reduced, the influence of γ-ray entering one radiation detector becomes negligible in X-ray CT examination.

$$W = 1 - exp(-T\alpha) \quad (2)$$

A description will be made of an example of the irradiation time period T of X-ray below. A specific irradiation time period T of X-ray has been determined based on Equations (1) and (2). The intensity of irradiation in the body caused by radio pharmaceutical administered to the examinee in the PET examination, is about 370 MBq at maximum (N=370 MBq) and the passing rate A of γ-rays in the body is about 0.6 (A=0.6) when the body of the examinee is assumed to be water having a radius of 15 cm. For example, assuming that the radiation detectors each having a side of 5 mm are arranged like a ring having a radius of 50 cm, the rate of incidence B calculated from the solid angle of one radiation detector is $8 \times 10^{-6}$ ($B = 8 \times 10^{-6}$). Further, the detection sensitivity C of the radiation detector is about 0.6 (C=0.6) at maximum when a semiconductor radiation detector is used. From these values, the detection rate α of γ-ray of one radiation detector is about 2000 (count/sec). When the irradiation time period T of X-ray is set to, for example, 1.5 μsec, the probability W of detection of γ-ray is 0.003 when one radiation detector is detecting X-rays and the γ-ray is almost negligible. In the case where the radioactivity administered to the body is made to be equal to or smaller than 360 MBq, when the irradiation time period of X-ray is made to be equal to or smaller than 1.5 μsec, W<0.003, that is, the probability of detection of γ-ray becomes equal to or smaller than 0.3%, which is negligible.

Also in the embodiment, similar to Embodiment 1, X-ray CT examination and PET examination are carried out. The X-ray CT examination and the PET examination according to the embodiment are also carried out by using the image pickup apparatus 2A in the state of inserting the examinee 34 into the hole portion 33 by moving the bed 16 on which the examinee 34 administered with the PET pharmaceutical is laid. The radiation detectors 4B and 4C detect both X-rays transmitted through the examinee 34 and γ-rays emitted from the examinee 34 caused by the PET pharmaceutical. The processing of the X-ray image signal and the γ-ray image signal from the radiation detector 4B at the signal discriminating apparatus 21 is the same as that in Embodiment 1.

The embodiment employs the above-described principle and differs from Embodiment 1. An explanation will mainly be made of the processing of the X-ray image signal in X-ray CT examination. Switching operation for connecting the movable terminal 44 of the changeover switch 43 to either of the fixed terminals 45 and 56 is based on a switch control signal which is an output from the drive controller 17 similarly to the change-over switch 22. The drive controller 17 selects the radiation detector 4A included in the first radiation detector and connects the movable terminal 44 of the changeover switch 43 in the X-ray signal processing apparatus 20A connected to the selected radiation detector 4A to the fixed terminal 45. A first set time period for connecting the movable terminal 44 to the fixed terminal 45 is set to, for example, 1 μsec so that the probability of detection of γ-rays at the radiation detector 4C can be disregarded. Therefore, the X-ray image signal from the radiation detector 4C is inputted to the X-ray intensity calculating apparatus 47 via the movable terminal 44 and the fixed terminal 45. The X-ray intensity calculating apparatus 47 outputs a current value of the X-ray image signal, that is, information on intensity of the X-ray image signal by a differential circuit. When the radiation detector 4C that has outputted the X-ray image signal becomes the second radiation detector, control of the drive controller 17 connects the movable terminal 44 to the fixed terminal 46. Therefore, even when the radiation detector 4C detects γ-rays emitted from the examinee 34 and outputs a γ-ray image signal, the γ-ray image signal is not inputted to the X-ray intensity calculating apparatus 47. Information on the intensity of the X-ray image signal outputted from the respective X-ray intensity calculating apparatus 47 is inputted to the computer 30. The computer 30 can form data of synthesized tomographic images synthesized with data of X-ray CT images and data of PET images based on the above-described processing procedure of FIG. 5.

The X-ray signal processing apparatus 20A is an X-ray image signal processing apparatus for selectively processing the X-ray image signal. The X-ray image signal processing apparatus is provided with the changeover switch 43 which is an X-ray image signal selecting apparatus for selecting the X-ray image signal by being controlled by the drive controller 17 and the X-ray intensity calculating apparatus 47 which is an X-ray image signal intensity information generating apparatus for outputting intensity information on the X-ray image signal by processing the X-ray image signal selected by the X-ray image signal selecting apparatus.

Also in the embodiment, the effects (1), (3) through (9) produced by Embodiment 1 can be achieved.

(Embodiment 3)

Figure 7:
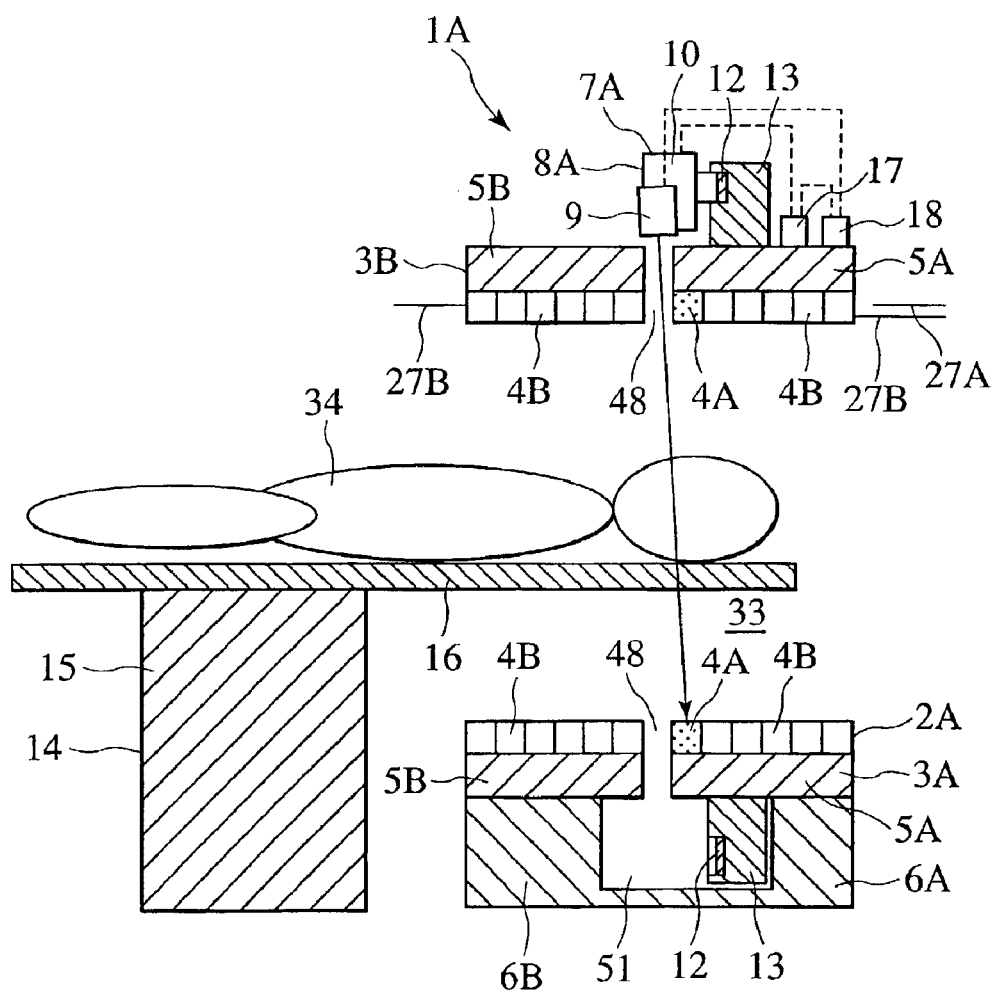
FIG. 7 is a constitution view of a radiological imaging apparatus of Embodiment 3, which is another embodiment of the invention.
Figure 8:
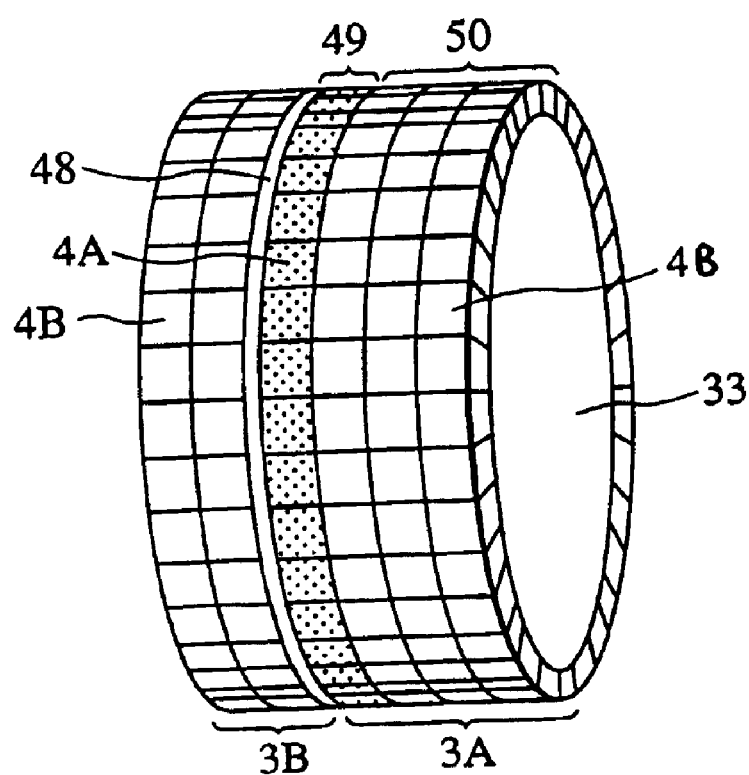
FIG. 8 is a perspective view showing an alignment of radiation detectors in a group of circular radiation detectors of FIG. 7.

A description will be made of a radiological imaging apparatus of Embodiment 3 with reference to FIG. 7 below, which is another embodiment of the invention. A radiological imaging apparatus 1A of the embodiment has a constitution in which the image pickup apparatus 2 in the radiological imaging apparatus 1 is changed to an image pickup apparatus 2A. Other constitutions in the radiological imaging apparatus 1A are the same as those of the radiological imaging apparatus 1. The image pickup apparatus 2A is provided with pluralities of groups of circular radiation detectors 3A and 3B. The groups of the circular radiation detectors 3A and 3B are provided with pluralities of rows of the circular radiation detectors arranged in the axial direction of the hole portion 33. Each of the circular rows of radiation detectors is provided with a plurality of radiation detectors disposed in the ring-like manner. On each of inner sides of the respective radiation detectors in the groups of circular radiation detectors 3A and 3B, the penetrating hole portion 33 to which the bed 16 is inserted is formed. The group of circular radiation detectors 3A and the group of circular radiation detectors 3B are contiguous to each other with a slit 48 interposed therebetween. The group of circular radiation detectors 3A is provide with a large number of radiation detectors constituting the plurality of circular rows of detectors on an inner side of a circular holding portion 5A similarly to Embodiment 1. As shown by FIG. 8, one row of the circular rows of radiation detectors 49 on a side of the slit 48 is provided with only a plurality of radiation detectors 4A arranged in the conferential direction of the hole portion 33 as radiation detectors constituting the row. All radiation detectors constituting other circular rows of radiation detectors 50 in the group of circular radiation detectors 3A are radiation detectors 4B. Also the group of circular radiation detectors 3B is provided with a large number of radiation detectors constituting a plurality of circular rows of radiation detectors on an inner side of a circular holding portion 5B. All radiation detectors included in all circular rows of radiation detectors in the group of circular radiation detectors 3B are the radiation detectors 4B. The circular holding portion 5A is mounted to a support member 6A installed at a casing (not illustrated) of the image pickup apparatus 2A. The circular holding portion 5B is also mounted to a support member 6B installed at the casing. An axial center of the group of circular radiation detectors 3A and an axial center of the group of circular radiation detectors 3B coincide with each other. The circular holding portions 5A and 5B are the same in inner diameter and in outer diameter. A total of axial lengths of the groups of the circular radiation detectors 3A and 3B in the hole portion 33 is the same as a length of rows of radiation detectors in the axial direction of the hole portion 33 of the image pickup apparatus 2 according to Embodiment 1 and is the same as the length of the image pickup apparatus for PET of the prior art.

The radiation detectors 4A of the group of circular radiation detectors 3A are connected to the respective separate X-ray signal processing apparatus 20 by the wiring 27A. The respective radiation detectors 4B of the groups of circular radiation detectors 3A and 3B are connected to the movable terminal 23 of the separate signal discriminating apparatus 21 by the wiring 27B.

Further, the image pickup apparatus 2A is provided with an X-ray source apparatus 8A and an X-ray source circumferential direction moving apparatus 7A having the circular X-ray source apparatus holding portion 13. The X-ray source apparatus holding portion 13 has the same configuration as that of Embodiment 1 and is attached to an outer face of the circular holding portion 5A. The X-ray source apparatus 8A includes the X-ray source 9 and the X-ray source drive apparatus 10 and is not provided with the axial direction moving arm 11. According to the embodiment, the X-ray source 9 is disposed on outer sides of the circular holding portions 5A and 5B and is opposed to the circular gap 48. The X-ray source 9 is attached to the casing of the X-ray source drive apparatus 10 to be inclined to the axial direction of the hole portion 33 such that an emitting port of X-ray is directed in a direction of the radiation detector 4A disposed on a side opposite to the X-ray source 9 by 180° at the radiation detector 4A inside the row of circular radiation detectors 49.

Also according to the embodiment, similarly to Embodiment 1, PET examination and X-ray CT examination are carried out by using a single piece of the image pickup apparatus. Similarly to Embodiment 1, the PET examination according to the embodiment is carried out by detecting γ-rays emitted from the examinee 34 caused by the radio pharmaceutical by the radiation detector 4B included in the second radiation detector. Further, the X-ray CT examination is carried out by turning the X-ray source apparatus 8A around the examinee 34 along the guide rail 12 similarly to the case of turning the X-ray source apparatus 8 in Embodiment 1. In the PET examination and the X-ray CT examination, the examinations are carried out by moving the examinee 34 in the axial direction of the hole portion 33 by moving the bed 16. According to the embodiment, in order to turn the X-ray source apparatus 8A smoothly, a space 51 is defined between the support member 6B and the X-ray holding portion 13 on an outer side of the circular holding portion 5A. The X-ray source apparatus 8A passes the space 51 in turning. According to the embodiment, X-rays emitted from the inclined X-ray source 9 and passing the circular gap 48 are irradiated in a direction inclined to the examinee 32 laid on the bed 16 and transmitted slantly in the body of the examinee 34. The transmitted X-rays are detected by the radiation detectors 4A and 4B included in the first radiation detector. According to the embodiment, the first radiation detector is disposed on the side of the slit 48 of the group of circular radiation detectors 3A opposed to the X-ray source 9. The X-rays are widely emitted from the X-ray source 9 and therefore, the first radiation detector 4 is present also at circular rows of radiation detectors including the radiation detector 4B contiguous to the row of the circular radiation detectors 49 inside the group of circular radiation detectors 3A, as well as circular rows of radiation detectors including the radiation detector 4B on the side of the slit 48 in the group of circular radiation detectors 3B. The first radiation detector is moved in the circumferential direction of the hole portion 33 similarly to Embodiment 1 in accordance with turning of the X-ray source 9.

The X-ray image signals outputted from the radiation detectors 4A and 4B included in the first radiation detectors are processed similarly to Embodiment 1. The intensity information on the X-ray image signal outputted from the X-ray signal processing apparatus 20 is inputted to the computer 30. The γ-ray image signal outputted from the radiation detector 4B included in the second radiation detector is processed by the signal discriminating apparatus 21 similarly to Embodiment 1. The computer 30 forms data of the synthesized tomographic images by carrying out the processing shown in FIG. 5 similarly to Embodiment 1. According to the embodiment, the X-ray CT image is provided by using the X-ray image signal with respect to X-rays slantly transmitted through the body of the examinee 35 and therefore, the X-ray source 9 needs to be inclined by an angle by which accuracy of the X-ray CT image is not deteriorated.

By carrying out PET examination by simultaneously using the group of circular radiation detectors 3A and the group of the circular radiation detectors 3B, also an area of the slit 48 interposed by the two detector groups and the row of circular radiation detectors 49 can substantially be subjected to PET examination. Specifically, by simultaneously counting γ-rays between the radiation detector 4B in the group of circular radiation detectors 3A and the radiation detector 4B in the group of circular radiation detectors 3B and converting the count into data, data is obtained which slantly traverses the area defined by the slit 48 and the row of circular radiation detectors 49 (an area where the radiation detector 4B for detecting γ-rays is not installed). By carrying out interpolation processing using the data, two-dimensional section PET images with regard to the area defined by the slit 48 and the row of circular radiation detectors 49 can be obtained.

The PET examination according to the embodiment can also be carried out independently by individually using the group of circular radiation detectors 3A and the group of the circular radiation detectors 3B.

The embodiment can achieve the effects of (1) through (7) produced by Embodiment 1. Further, the embodiment can achieve the following effects of (10) through (13).

(10) Since the X-ray source 9 is turned on the outer side of the group of circular radiation detectors 3A and therefore, diameters of the circular holding portions 5A and 5B are reduced. Therefore, a distance between two of the radiation detectors disposed just oppositely to each other by 180° is shortened to improve image quality of the PET image. The pair of γ-rays generated in the body of the examinee 34 is emitted in directions opposed to each other not completely by 180° but 180°±0.6°. When the distance between the radiation detectors is extended, the influence of ±0.6° is increased and two detecting points with regard to the pair of γ-rays specified by the simultaneous counting apparatus 28 are more or less shifted from each other. When the distance between the radiation detectors is shortened, the influence of ±0.6° is reduced and two detecting points with regard to the pair of γ-rays specified by the simultaneous time counting apparatus 28 become proximate to true positions. Thus, according to the embodiment, the image quality of the PET image is enhanced.

(11) According to the embodiment, the X-ray source 9 is turned on the outer side of the group of circular radiation detectors 3A and therefore, there is not present such an object of blocking γ-rays emitted from the examinee 34 on the front side of the radiation detector as the X-ray source 9 and the axial direction moving arm 11 in Embodiment 1. Therefore, according to the embodiment, the problem does not arise that detected data is deficient as in Embodiment 1.

(12) The radiological imaging apparatus can further be downsized as compared with that of Embodiment 1 since the outer shape of the group of circular radiation detectors is reduced.

(13) According to the embodiment, the row of circular radiation detectors 49 is provided with only the radiation detector 4A as the radiation detector for detecting X-rays and an alignment pitch of the radiation detector 4A in the row 49 can be made smaller than an alignment pitch of the radiation detector 4B in other circular rows of radiation detectors. Therefore, resolution of X-ray CT examination can be enhanced.

According to the embodiment, the row of circular radiation detectors including only the radiation detector 4A as the radiation detector may be disposed on the side of the slit 48 in the group of circular radiation detectors 3B and may be attached to the casing of the X-ray drive apparatus 10 to be inclined to the axial direction of the hole portion 33 so that the irradiation port of X-ray at the X-ray source 9 is directed in a direction of the radiation detector 4A disposed on a side of the radiation detector 4A opposed to the X-ray source 9 by 180° in the group of circular radiation detectors 3B. Further, the X-ray source apparatus holding portion 13 may be attached to the circular holding portion 5B and inclined such that the emitting port of X-ray of the X-ray source 9 is directed to the radiation detector 4A of the group of circular radiation detectors 3A as described above. Further, all the radiation detectors of the groups of circular radiation detectors 3A and 3B of the embodiment may be constituted by the radiation detectors 4B and the radiation detectors 4B in the row of circular radiation detectors 49 may be connected to the X-ray signal processing apparatus 20A shown in FIG. 6 similarly to Embodiment 2.

The group of circular radiation detectors 3B and the slit 48 may be removed from the embodiment and the row of circular radiation detectors 49 may be disposed at a position most proximate to the examinee holding apparatus 19. In this case, examination of the total body by X-ray CT may be carried out in moving the examinee for examination of the total body of the PET examination. With this constitution, a moving distance and a moving time period of the examinee in shifting from X-ray CT examination to PET examination can be minimized.

(Embodiment 4)

Figure 9:
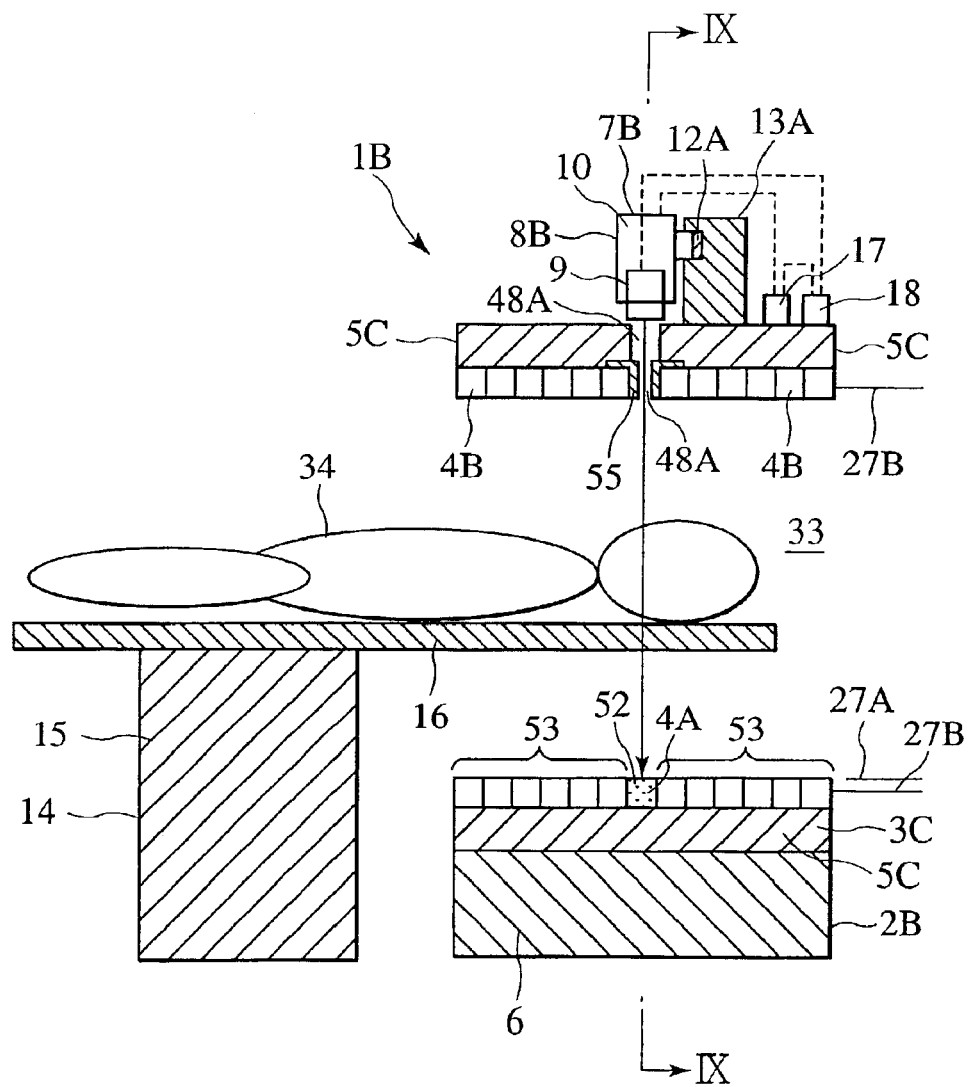
FIG. 9 is a constitution view of a radiological imaging apparatus of Embodiment 4, which is another embodiment of the invention.
Figure 10:
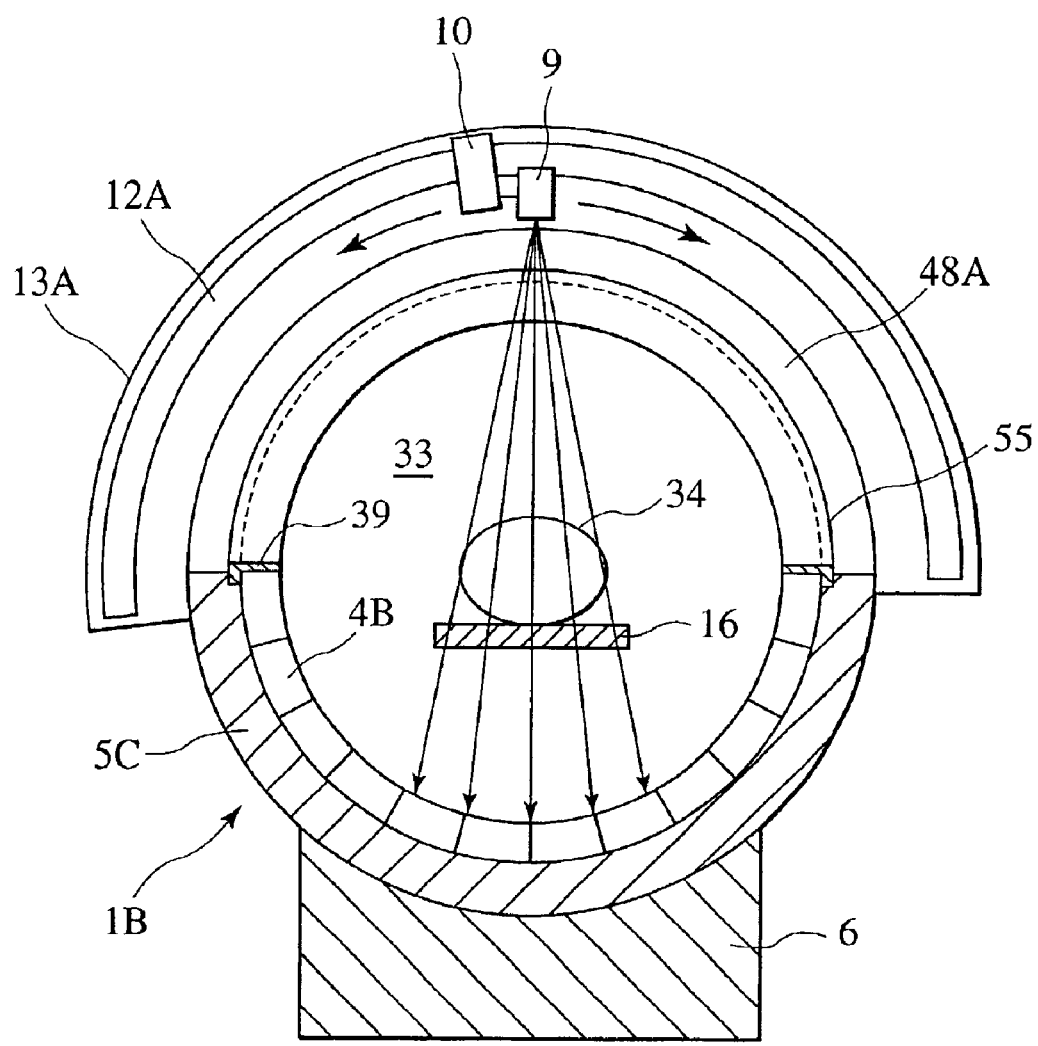
FIG. 10 is a sectional view taken along line IX—IX of FIG. 9.

A description will be made of a radiological imaging apparatus 1B of Embodiment 4, which is another embodiment of the invention in reference to FIGS. 9 and 10. The radiological imaging apparatus 1B is provided with an image pickup apparatus 2B and the constitutions thereof other than the image pickup apparatus 2B are the same as those of the radiological imaging apparatus 1. A description will be given of a portion of the constitution of the radiological imaging apparatus 1B different from that of the radiological imaging apparatus 1. The image pickup apparatus 2B is provided with a group of circular radiation detectors 3C and an X-ray source circumferential direction moving apparatus 7B. The group of circular radiation detectors 3C is provided with a large number of radiation detectors constituting a plurality of circular rows of radiation detectors similarly to Embodiment 1 on an inner face of a circular holding portion 5C mounted to the holding member 6. The circular holding portion 5C is provided with a slit 48A that is a penetrating hole cut out over 180° in the circumferential direction. The slit 48A has a width equal to that of one radiation detector and is disposed at an upper half of the circular holding portion 5C. According to the group of circular radiation detectors 3C, a single row of a row of radiation detectors 52 disposed at the portion of the slit 28A includes only the radiation detector 4A as the radiation detector and a plurality of other circular rows of radiation detectors 53 includes the radiation detectors 4B as the radiation detectors. The row of radiation detectors 52 does not include radiation detectors disposed at the portion of the slit 48A but include the radiation detectors 4A disposed at an area of about 180° excluding the portion of the slit 48A. The row of circular radiation detectors 53 includes the radiation detectors 4B disposed at a portion over an area of 360° around the hole portion 33. A collimator 55 formed of lead is provided at the portion of the slit 48A on an inner side of the circular holding portion 5C. The radiation detectors 4A and 4B are disposed on an outer side of the collimator 55. The radiation detector 4A is connected to the X-ray signal processing apparatus 20 (FIG. 1) via the wiring 27A and the radiation detector 4B is connected to the signal discriminating apparatus 21 (FIG. 1) via the wiring 27B.

The X-ray source peripheral direction moving apparatus 7B is provided with an X-ray source apparatus holding portion 13A in a substantially semicircular shape and an X-ray source apparatus 8B. The X-ray source apparatus holding portion 13A provided with a semicircular guide rail 12A is mounted on an outer side of the circular holding member 5C. The X-ray source apparatus 8B is provided with an X-ray source 8C having an X-ray source 9 and an X-ray source drive apparatus 10. The X-ray source apparatus 8B mounts the X-ray source 9 on the X-ray source drive apparatus 10 such that the X-ray emitting port of the X-ray source 9 is directed orthogonally to the axial center of the hole portion 33 and in the direction of the radiation detector 4A of the row of radiation detectors 52.

Also in this embodiment, the examinee 34 administered with PET pharmaceutical and laid on the bed 16 is subjected to PET examination and X-ray CT examination by using a single piece of the image pickup apparatus 2B. In the PET examination and X-ray CT examination, similarly to Embodiment 3, the examinations are carried out by moving the examinee 34 in the axial direction. The X-ray CT examination is carried out by irradiating the examinee 34 with X-rays emitted from the X-ray source 9 and allowed to pass through the slit 48A and the collimator 55. According to the embodiment, similarly to Embodiment 1, the PET examination is carried out by detecting γ-rays emitted from the examinee 34 with the radiation detector 4B included in the second radiation detector and X-ray CT examination is carried out by detecting X-rays transmitted through the examinee 34 with the radiation detector 4A included in the first radiation detector. Processing of the X-ray image signal outputted from the radiation detector 4A and the X-ray image signal and the γ-ray image signal outputted from the radiation detector 4B are carried out similarly to Embodiment 1 and the synthesized examinee image data is formed by the computer 30.

In the X-ray Ct examination according to the embodiment, by moving the X-ray source drive apparatus 10 along the guide rail 12A, the X-ray source 9 is moved around the examinee 34 in a range of 180° and the X-ray image signal is obtained by the radiation detector included in the first radiation detector. The X-ray signal processing apparatus 20 receives the X-ray image signal from the radiation detector 4A so s to obtain the intensity information on the X-ray image signal. The computer 30 obtains the two-dimensional section data of the X-ray CT images by using the intensity information. The other two-dimensional section data can be formed by using the X-ray image signal provided by moving the examinee 34 in the axial direction of the hole portion 33 and moving the X-ray source 9 along the guide rail 12A. The three-dimensional section data of the X-ray CT images can be obtained by piling up the two-dimensional section data.

According to the embodiment, the effects of (1) through (7) produced by Embodiment 1 and the effects of (11) through (13) produced by Embodiment 3 can be achieved. Further, the embodiment can achieve the following effect of (14).

(14) The radiation blocking function of the collimator 55 can block X-rays entering the radiation detectors 4A and 4B contiguous to the collimator 55.

The row of radiation detectors 52 may be disposed at a position of a row of radiation detectors most proximate to the examinee holding apparatus 14 among rows of radiation detectors in the axial direction of the group of circular radiation detectors 3C. In this case, it is necessary to change a position of installing the X-ray source circumferential direction moving apparatus 7B such that also the X-ray source 9 is disposed at the position. Further, all radiation detectors of the group of circular radiation detectors 3C may be constituted as the radiation detectors 4B and the radiation detectors 4B in the row of radiation detectors 52 may be connected with the X-ray signal processing apparatus 20A shown in FIG. 6 similarly to Embodiment 2.

(Embodiment 5)

Figure 11:
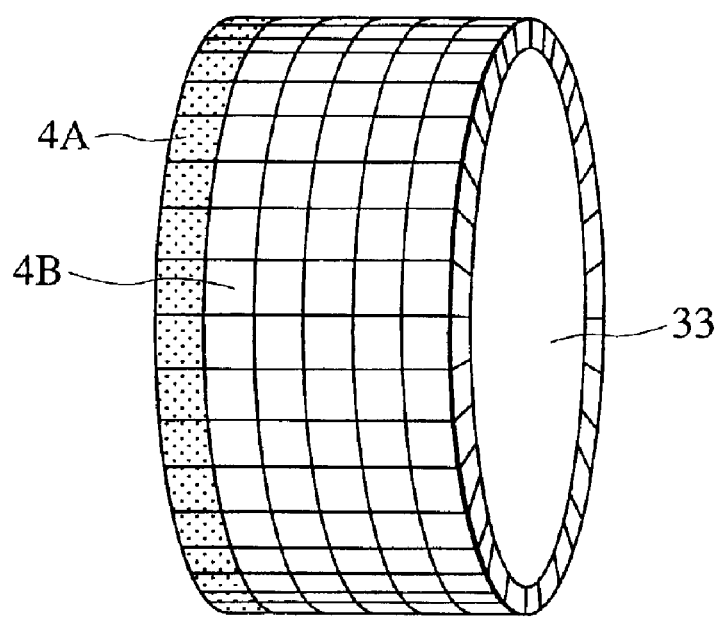
FIG. 11 is a perspective view showing an alignment of radiation detectors in a group of circular radiation detectors in a radiological imaging apparatus of Embodiment 5, which is another embodiment of the invention.

A description will below be made of a radiological imaging apparatus of Embodiment 5, which is other embodiment of the invention. The embodiment has a constitution in which arrangement of the radiation detectors 4A and 4B is changed in Embodiment 1. That is, as shown in FIG. 11, one row of circular radiation detectors on the side of the examinee holding apparatus 14 includes only the radiation detector 4A as the radiation detector and a plurality of other circular rows of radiation detectors 53 includes only the radiation detectors 4B as the radiation detectors. The other constitutions of the embodiment are similar to those of Embodiment 1. X-ray CT examination and PET examination, processing of output signals from the radiation detectors 4A and 4B and processing of forming the synthesized tomographic image data in the computer 30 are carried out similarly to Embodiment 1. The embodiment can achieve the effects of (1) through (9) obtained in Embodiment 1.

(Embodiment 6)

Figure 12:
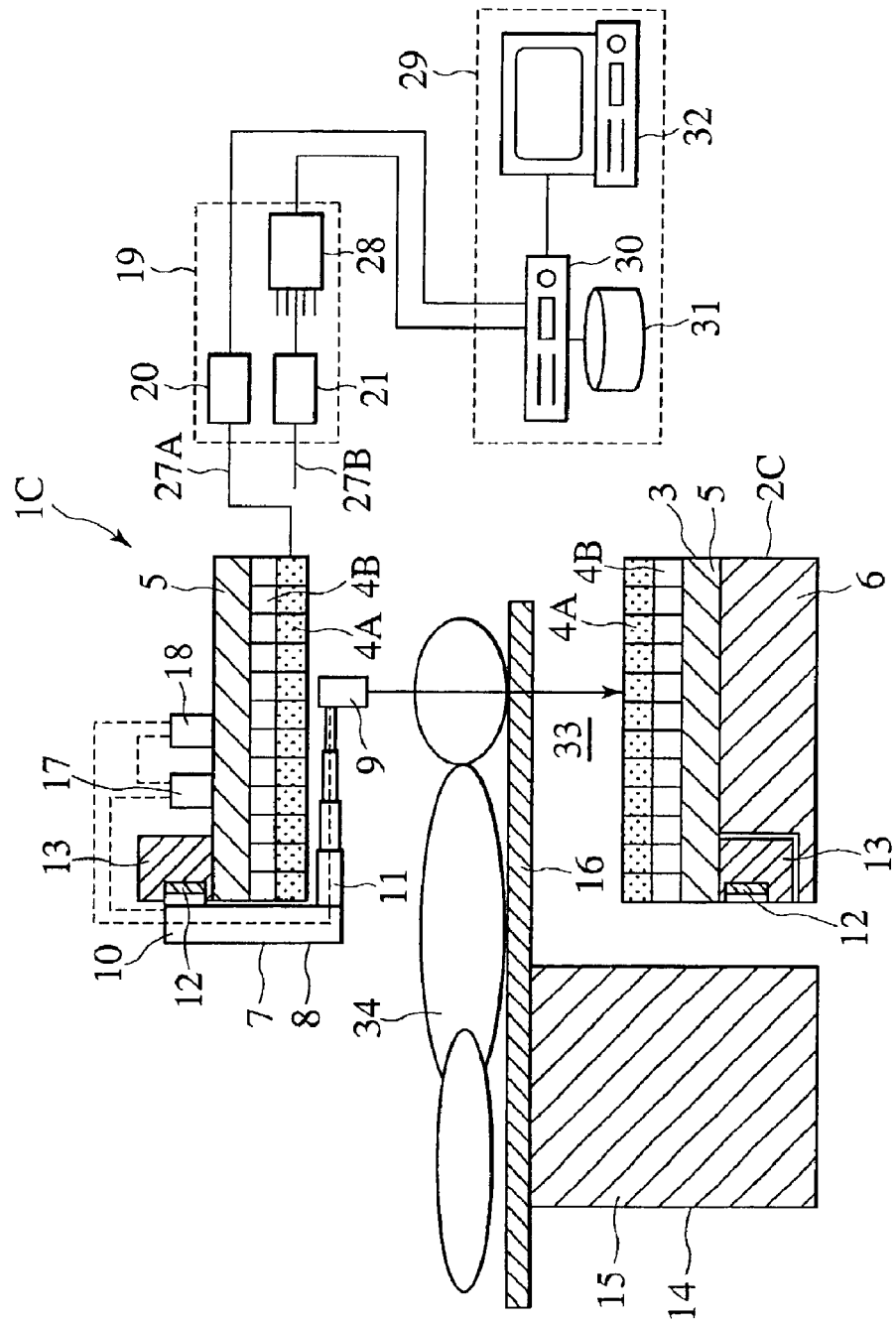
FIG. 12 is a constitution view of a radiological imaging apparatus of Embodiment 6 which is other embodiment of the invention.

A description will below be made of a radiological imaging apparatus 1C of Embodiment 6, which is another embodiment of the invention in reference to FIG. 12. According to the radiological imaging apparatus 1C, the image pickup apparatus 2 of the radiological imaging apparatus 1 is changed to an image pickup apparatus 2C and the other constitutions are the same as those of the radiological imaging apparatus 1. The image pickup apparatus 2C is configured by changing arrangement of rows of radiation detectors in the image pickup apparatus 2. The other constitutions of the image pickup apparatus 2C are the same as those of the image pickup apparatus 2. A description will be given of the arrangement of rows of radiation detectors of the image pickup apparatus 2C. According to the embodiment, a number of the radiation detectors 4A are arranged on inner sides of a number of the radiation detectors 4B and the radiation detector 4A and the radiation detector 4B are arranged to layer linearly in the radial direction of the hole portion 33. Specifically a single piece of the radiation detector 4A and a single piece of the radiation detector 4B are arranged to layer in a paired manner and the radiation detector 4B is disposed on the outer side of the radiation detector 4A. The radiation detectors 4A and 4B are arranged circularly in the circumferential direction of the hole portion 33 and pluralities of rows thereof are arranged also in the axial direction. According to the embodiment, the respective rows of the circular radiation detectors include the radiation detectors 4A and 4B. The radiation detectors 4A and 4B are provided in the circular holding portion 5. The radiation detector 4A is connected to the X-ray signal processing apparatus 20 with the wiring 27A. The radiation detector 4B is connected to the signal discriminating apparatus 21 with the wiring 27B.

Also in the embodiment, the examinee 34 administered with PET pharmaceutical and laid on the bed 16 is subjected to the PET examination and the X-ray CT examination by using a single piece of the image pickup apparatus 2C. The X-ray CT examination is carried out by irradiating the examinee 34 with X-rays emitted from the X-ray source 9 and X-rays transmitted through the examinee 34 is detected with the radiation detector 4A included in the first radiation detector. The PET examination is carried out by detecting γ-rays emitted from the examinee 34 with the irradiation detector 4B included in the second irradiation detector. X-rays having low energy (80 keV) is detected with the radiation detector 4A at a first layer and γ-rays having high energy (511 keV) passes the radiation detector 4A at the first layer almost nonreactively and can be detected with the radiation detector 4B at a second layer. The X-ray image signal outputted from the radiation detector 4A is processed by the X-ray signal processing apparatus similarly to Embodiment 1. The γ-ray image signal outputted from the radiation detector 4B is processed by the signal discriminating apparatus 21 similarly to Embodiment 1. The synthesized tomographic image data is formed by the computer 30 similarly to Embodiment 1.

The embodiment can achieve the effects of (1) through (9) produced by Embodiment 1.

In the embodiment, it is possible to constitute an arrangement of circular rows of radiation detectors in which the first layer of the radiation detectors 4A and the second layer of the radiation detectors 4B are arranged to layer only at portions of circular rows of radiation detectors in the axial direction of the hole portion 33 (for example, one row of circular radiation detectors mostly proximate to the examinee holding apparatus 14) and other circular rows of radiation detectors do not include the radiation detectors 4A but include the radiation detectors 4B.

(Embodiment 7)

Figure 13:
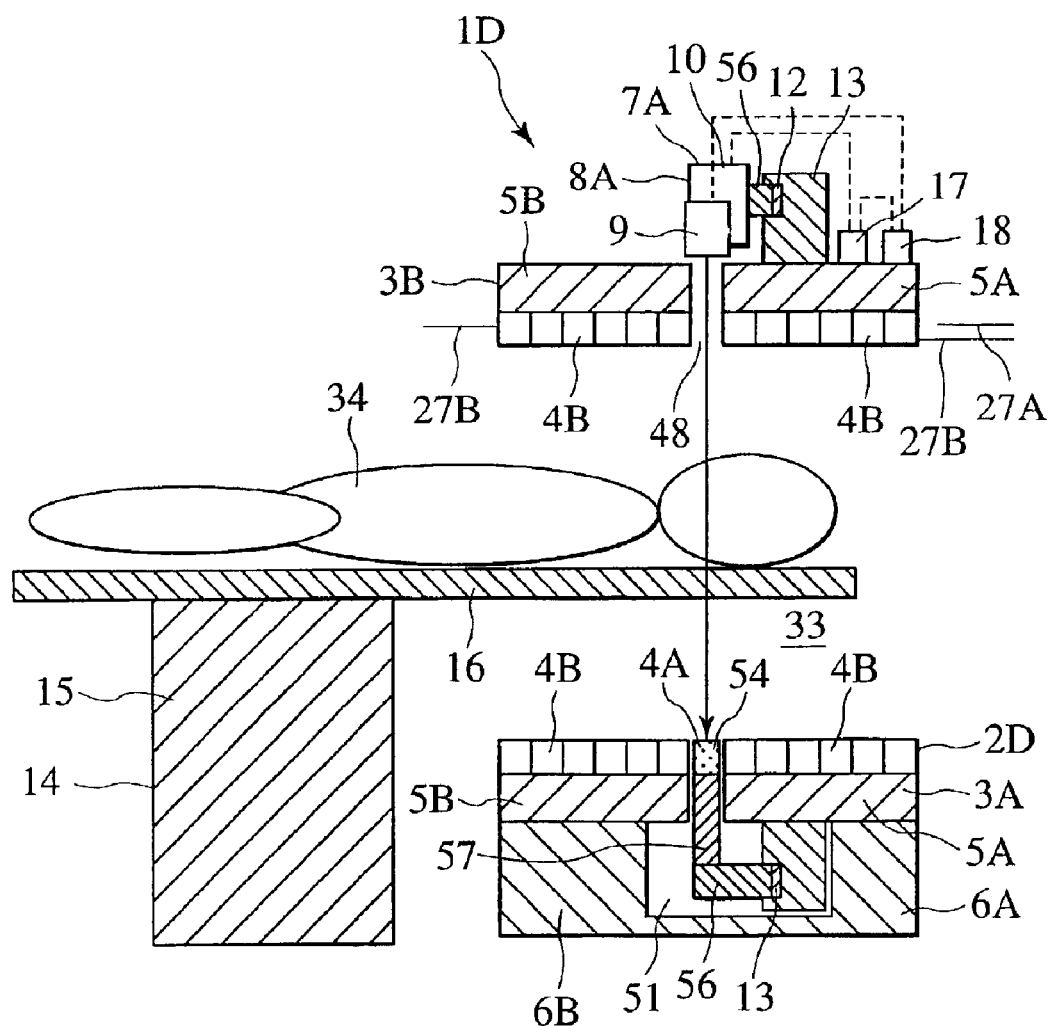
FIG. 13 is a constitution view of a radiological imaging apparatus of Embodiment 7, which is another embodiment of the invention.

A description will below be made of a radiological imaging apparatus 1D of Embodiment 7, which is another embodiment of the invention in reference to FIG. 13. According to the radiological imaging apparatus 1D, the image pickup apparatus 2A of the radiological imaging apparatus 1A is changed to an image pickup apparatus 2D and other constitutions are the same as those of the radiological imaging apparatus 1A. According to the image pickup apparatus 2D, a mounting position of the radiation detector 4A in the image pickup apparatus 2A is changed. The other constitutions of the image pickup apparatus 2D are the same as those of the image pickup apparatus 2A. An explanation will be given of a structure of mounting the radiation detector 4A in the image pickup apparatus 2D.

The image pickup apparatus 2D is provided with an X-ray source circumferential direction moving apparatus 7D and the circular holding portion 5A is not provided with the radiation detector 4A. That is, the groups of circular radiation detectors 3A and 3B each do not include the radiation detector 4B. According to the embodiment, the X-ray source circumferential direction moving apparatus 7D includes the radiation detector 4D. The X-ray source peripheral direction moving apparatus 7D is provided with a circular connecting portion 56 surrounding the circular holding portion 5A and the X-ray source drive apparatus 10 of the X-ray source apparatus 8A is mounted to the circular connecting portion 56. A plurality of the radiation detectors 4A arranged in the circumferential direction of the hole portion 33 are attached to a holding member 57 a portion of which is inserted into the slit 48. The respective radiation detectors 4A are disposed in the slit 48. The radiation detectors 4A are disposed in a range capable of covering the spreading width in the shape of the fan beam emitted from the X-ray source 9. According to the embodiment, it is not necessary to arrange the X-ray source 9 slantly as in Embodiment 3.

The PET examination is carried out similarly to Embodiment 3. In carrying out X-ray CT examination, the circular connecting portion is turned around the circular holding portion 5A along the guide rail 12 by operation of the X-ray source drive apparatus 10. In conformity with the movement, the X-ray source 9 and the radiation detector 4A is moved around the examinee 34. The radiation detector 4A is moved in the circumferential direction in the slit 48. X-rays emitted from the X-ray source 9 and transmitted through the examinee 34 is measured by the respective irradiation detector 4A. Also according to the embodiment, data of synthesized tomographic images can be obtained similarly to Embodiment 1. The embodiment can achieve the effects of (1) through (7) and (10) through (13). Further, the radiation detector 4A is not arranged parallel to the radiation detector 4B as in the embodiment, but may be disposed at a position on outer sides of the circular holding portions 5A and 5B, that is, within a space 51.

According to the present invention, the radiological imaging apparatus capable of carrying out radiological imaging of the subject using X-rays and γ-rays can be simplified.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A radiological imaging apparatus comprising:
   a bed on which a subject is laid;
   an image pickup apparatus;
   the image pickup apparatus comprising:
     an X-ray source which is used to irradiate the subject with X-rays;
     an X-ray source moving apparatus for moving the X-ray source in a circumferential direction of a hole portion into which the bed is inserted;
     a plurality of first radiation detectors, disposed around the hole portion, for not substantially detecting γ-rays from the subject but detecting X-rays, and outputting a first detecting signal which is a detecting signal of X-rays; and
     a second radiation detector, disposed around the hole portion, for detecting γ-rays and X-rays from the subject and outputting both the first detecting signal and a second detecting signal which is a detecting signal of γ-rays;
   a first signal processing apparatus for processing the first detecting signal outputted from the first radiation detector; and
   a second signal processing apparatus for processing the second detecting signal outputted from the second radiation detector.

2. The radiological imaging apparatus according to claim 1 wherein the X-ray source is moved in a circumferential direction of the hole portion along a line nearer a center of the hole portion than the first radiation detector and the second radiation detector.

3. The radiological imaging apparatus according to claim 2 wherein a plurality of circular rows of radiation detectors including the first radiation detector and the second radiation detector and surrounding the hole portion are disposed in an axial direction of the hole portion.

4. The radiological imaging apparatus according to claim 2 wherein a group of circular radiation detectors are formed by arranging a plurality of circular rows of radiation detectors having pluralities of radiation detectors arranged to surround the hole portion in an axial direction of the hole portion; and
   wherein among the plurality of circular rows of radiation detectors, a portion of the circular rows of radiation detectors includes a plurality of the first radiation detectors only as the radiation detectors and remaining ones of the circular rows of radiation detectors include a plurality of the second radiation detectors only as the radiation detectors.

5. The radiological imaging apparatus according to claim 1 wherein the X-ray source is moved in the circumferential direction of the hole portion on outer sides of the first radiation detector and the second radiation detector.

6. The radiological imaging apparatus according to claim 5 wherein a group of circular radiation detectors are formed by arranging a plurality of circular rows of radiation detectors having pluralities of radiation detectors arranged to surround the hole portion in an axial direction of the hole portion;

wherein a gap for allowing X-rays emitted from the X-ray source to pass therethrough is defined in the group of rink-like radiation detectors; and wherein among the plurality of circular rows of radiation detectors, a portion of the circular rows of radiation detectors includes a plurality of the first radiation detectors only as the radiation detectors and disposed contiguously to the gap, and remaining ones of the circular rows of radiation detectors include a plurality of only the second radiation detectors as the radiation detectors.

7. The radiological imaging apparatus according to claim 5 wherein a group of circular radiation detectors is formed by arranging a plurality of circular rows of radiation detectors having pluralities of radiation detectors arranged to surround the hole portion in an axial direction of the hole portion;

wherein a gap for allowing X-rays emitted from the X-ray source to pass therethrough is defined in the group of circular radiation detectors; and wherein a row of radiation detectors including a plurality of the first radiation detectors only as the radiation detectors in a circumferential direction of the hole portion is disposed on a circular member on which the X-ray source is disposed, opposite to the X-ray source, the first radiation detectors are moved in a circumferential direction of the gap for allowing X-rays to pass therethrough along with movement of the X-ray source and remaining ones of the circular rows of radiation detectors include a plurality of the second radiation detectors only as the radiation detectors.

8. The radiological imaging apparatus according to claim 1, wherein the first radiation detector is disposed at an inner side from the second radiation detector in a radial direction of said hole portion.

9. The radiological imaging apparatus according to claim 8 wherein the first radiation detector and the second radiation detector are disposed in line in a radial direction of the hole portion.

10. The radiological imaging apparatus according to claim 1 wherein the radiation detector is a semiconductor radiation detector.

11. The radiological imaging apparatus according to claim 1, further comprising a tomographic image data forming apparatus for forming data of a first tomographic image of the subject based on first information outputted from the first signal processing apparatus by processing the first detecting signal, forming data of a second tomographic image of the subject based on second information outputted from the second signal processing apparatus by processing the second detecting signal, and forming data of a synthesized tomographic image caused by a combination of the data of the first tomographic image and the data of the second tomographic image.

12. The radiological imaging apparatus according to claim 11 wherein the first tomographic image is PET image.

13. A radiological imaging apparatus comprising:
a bed on which a subject is laid;
an image pickup apparatus, wherein the image pickup apparatus comprises:
an X-ray source which irradiates the subject with X-rays;
a plurality of first radiation detectors, disposed around a hole portion into which the bed is inserted, for detecting γ-rays and X-rays from the subject and outputting both a first detecting signal which is a detecting signal of X-rays and a second detecting signal which is a detecting signal of γ-rays;
a second radiation detector, disposed around the hole portion, for detecting γ-rays and X-rays from the subject and outputting both the first detecting signal and the second detecting signal;
wherein a group of circular radiation detectors are formed by arranging, in an axial direction of the hole portion, a plurality of circular rows of radiation detectors, each row including a plurality of radiation detectors arranged to surround the hole portion;
wherein a gap for allowing X-rays emitted from the X-ray source to pass therethrough extends in a circumferential direction of the hole portion and forms said group of circular radiation detectors;
wherein among the plurality of circular rows of radiation detectors, a portion of the circular rows of radiation detectors includes a plurality of only the first radiation detectors as the radiation detectors and disposed contiguously to the gap, and remaining ones of the circular rows of radiation detectors includes a plurality of only the second radiation detectors as the radiation detectors; and
an X-ray source moving apparatus for moving the X-ray source in the circumferential direction of the hole portion along said gap, said X-ray source being disposed outside of said first and second radiation detectors;
a first signal processing apparatus for processing the first detecting signal outputted from the first radiation detector; and
a second signal processing apparatus for processing the second detecting signal outputted from the second radiation detector.

14. The radiological imaging apparatus according to claim 13, wherein the first radiation detector is disposed at an inner side from the second radiation detector in a radial direction of said hole portion.

15. The radiological imaging apparatus according to claim 14 wherein the first radiation detector and the second radiation detector are disposed in line in a radial direction of the hole portion.

16. The radiological imaging apparatus according to claim 13, wherein the first and second radiation detectors are semiconductor radiation detectors.

17. The radiological imaging apparatus according to claim 13, further comprising a tomographic image, data forming apparatus for forming data of a first tomographic image, of the subject based on first information outputted from the first signal processing apparatus by processing the first detecting signal, forming data of a second tomographic image of the subject based on second information outputted from the second signal processing apparatus by processing the second detecting signal, and forming data of a synthesized tomographic image caused by a combination of the data of the first tomographic image and the data of the second tomographic image.

18. The radiological imaging apparatus according to claim 17, wherein the first tomographic image is an X-ray CT image and the second tomographic image is a PET image.

19. A radiological imaging apparatus comprising;
a bed on which a subject is laid;
an image pickup apparatus, wherein the image pickup apparatus comprises:
an X-ray source which irradiates the subject with X-rays;
a plurality of first radiation detectors, disposed around a hole potion into which the bed is inserted, for detecting trays and X-rays from the subject and outputting both a first detecting signal which is a detecting signal of X-rays and a second detecting signal which is a detecting signal of γ-rays;
a second radiation detector, disposed around the hole portion, for detecting γ-rays and X-rays from the subject and outputting both the first detecting signal and the second detecting signal;
wherein a group of circular radiation detectors are formed by arranging, in an axial direction of the hole portion, a plurality of circular rows of radiation detectors, each row including a plurality of radiation detectors arranged to surround the hole portion;
wherein a gap for allowing X-rays emitted from the X-ray source to pass therethrough extends in a circumferential direction of the hole portion and forms said group of circular radiation detectors;
wherein a row of radiation detectors including a plurality of only the first radiation detectors as the radiation detectors in the circumferential direction of the hole portion is disposed on a circular member on which the X-ray source is disposed, opposite to the X-ray source, and remaining ones of the circular rows of radiation detectors include a plurality of only the second radiation detectors as the radiation detectors; and
an X-ray source moving apparatus for moving the X-ray source in the circumferential direction of the hole portion along said gap and said first radiation detectors in the circumferential direction of the hole portion along said gap together with the movement of said X-ray source, said X-ray source being disposed at an outer side from said first and second radiation detectors;
a first signal processing apparatus for processing the first detecting signal outputted from the first radiation detector; and
a second signal processing apparatus for processing the second detecting signal outputted from the second radiation detector.

20. The radiological imaging apparatus according to claim 19, wherein the first radiation detector is disposed at an inner side from the second radiation detector in a radial direction of said hole portion.

21. The radiological imaging apparatus according to claim 20 wherein the first radiation detector and the second radiation detector are disposed in line in a radial direction of the hole portion.

22. The radiological imaging apparatus according to claim 19, wherein the first and second radiation detectors are semiconductor radiation detectors.

23. The radiological imaging apparatus according to claim 19, further comprising a tomographic image data forming apparatus for forming data of a first tomographic image of the subject based on first information outputted from the first signal processing apparatus by processing the first detecting signal, forming data of a second tomographic image of the subject based on second information outputted from the second signal processing apparatus by processing the second detecting signal, and forming data of a synthesized tomographic image caused by a combination of the data of the first tomographic image and the data of the second tomographic image.

24. The radiological imaging apparatus according to claim 23, wherein the first tomographic image is an X-ray CT image and the second tomographic image is a PET image.

25. A radiological imaging apparatus comprising:
a bed on which a subject is laid;
an image pickup apparatus, wherein the image pickup apparatus comprises:
an X-ray source which irradiates the subject with X-rays;
a plurality of first radiation detectors, disposed around a hole portion into which the bed is inserted, for detecting γ-rays and X-rays from the subject and outputting both a first detecting signal which is a detecting signal of X-rays and a second detecting signal which is a detecting signal of γ-rays;
a second radiation detector, disposed around the hole portion, for detecting γ-rays and X-rays from the subject and outputting both the first detecting signal and the second detecting signal;
a first X-ray source moving apparatus for moving the X-ray source in the circumferential direction of the hole portion at an inner side from said first and second radiation detectors, said X-ray source being disposed at an inner side from said first and second radiation detectors in a radial direction of the hole portion; and
a second X-ray source moving apparatus for moving the X-ray source in a longitudinal direction of the bed at an inner side from said first and second radiation detectors, said X-ray source being disposed at an inner aide from said first and second radiation detectors in a radial direction of the hole portion;
a first signal processing apparatus for processing the first detecting signal outputted from the first radiation detector; and
a second signal processing apparatus for processing the second detecting signal outputted from the second radiation detector.

26. The radiological imaging apparatus according to claim 25 wherein a plurality of circular rows of radiation detectors including the first radiation detector and the second radiation detector and surrounding the hole portion are disposed in an axial direction of the hole portion.

27. The radiological imaging apparatus according to claim 26 wherein a group of circular radiation detectors are formed by arranging a plurality of circular rows of radiation detectors having pluralities of radiation detectors arranged to surround the hole portion in an axial direction of the hole pardon; and
wherein among the plurality of circular rows of radiation detectors, a portion of the circular rows of radiation detectors includes a plurality of the first radiation detectors only as the radiation detectors and remaining ones of the circular rows of radiation detectors include a plurality of the second radiation detectors only as the radiation detectors.

28. The radiological imaging apparatus according to claim 25, wherein the first radiation detector is disposed at an inner side from the second radiation detector in a radial direction of said hole portion.

29. The radiological imaging apparatus according to claim 28 wherein the first radiation detector and the second radiation detector are disposed in line in a radial direction of the hole portion.

30. The radiological imaging apparatus according to claim 25 wherein the radiation detector is a semiconductor radiation detector.

31. The radiological imaging apparatus according to claim 25, further comprising a tomographic image data forming apparatus for forming data of a first tomographic image of the subject based on first information outputted from the first signal processing apparatus by processing the first detecting signal, forming data of a second tomographic image of the subject based on second information outputted from the second signal processing apparatus by processing the second detecting signal and forming data of a synthesized tomographic image caused by a combination of the data of the first tomographic image and the data of the second tomographic image.

32. The radiological imaging apparatus according to claim 31, wherein the first tomographic image is an X-ray CT image, and the second tomographic image is a PET image.

* * * * *